United States Patent
Gorski et al.

(10) Patent No.: US 10,156,562 B2
(45) Date of Patent: Dec. 18, 2018

(54) ASSAY FOR DETECTING TH1 AND TH2 CELL POPULATIONS

(71) Applicant: AMGEN INC., Thousand Oaks, CA (US)

(72) Inventors: Kevin Gorski, Newbury Park, CA (US); Jane R. Parnes, Agoura Hills, CA (US); Jeannette Bigler, Seattle, WA (US); Michael J. Boedigheimer, Newbury Park, CA (US); Andrew A. Welcher, Ventura, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/311,635

(22) PCT Filed: May 15, 2015

(86) PCT No.: PCT/US2015/030940
§ 371 (c)(1),
(2) Date: Nov. 16, 2016

(87) PCT Pub. No.: WO2015/175861
PCT Pub. Date: Nov. 19, 2015

(65) Prior Publication Data
US 2017/0082608 A1 Mar. 23, 2017

Related U.S. Application Data

(60) Provisional application No. 61/994,430, filed on May 16, 2014.

(51) Int. Cl.
G01N 33/533 (2006.01)
G01N 33/50 (2006.01)
G01N 33/58 (2006.01)

(52) U.S. Cl.
CPC ......... *G01N 33/505* (2013.01); *G01N 33/533* (2013.01); *G01N 33/582* (2013.01); *G01N 2333/4715* (2013.01); *G01N 2333/525* (2013.01); *G01N 2333/5406* (2013.01); *G01N 2333/5409* (2013.01); *G01N 2333/5437* (2013.01); *G01N 2333/55* (2013.01); *G01N 2333/57* (2013.01); *G01N 2800/52* (2013.01)

(58) Field of Classification Search
None
See application file for complete search history.

(56) References Cited

U.S. PATENT DOCUMENTS

| | | |
|---|---|---|
| 4,391,904 A | 7/1983 | Litman et al. |
| 4,816,567 A | 3/1989 | Cabilly et al. |
| 5,545,807 A | 8/1996 | Surani et al. |
| 5,585,089 A | 12/1996 | Queen et al. |
| 5,693,762 A | 12/1997 | Queen et al. |
| 6,039,969 A | 3/2000 | Tomai et al. |
| 6,143,874 A | 11/2000 | Chang |
| 6,184,359 B1 | 2/2001 | Grabstein et al. |
| 6,232,447 B1 | 5/2001 | Cerretti |
| 6,235,883 B1 | 5/2001 | Jakobovits et al. |
| 6,287,791 B1 | 9/2001 | Terstappen et al. |
| 6,319,499 B1 | 11/2001 | Elliott |
| 6,355,779 B1 | 3/2002 | Goodwin et al. |
| 6,500,429 B2 | 12/2002 | Boone et al. |
| 6,596,852 B2 | 7/2003 | Cerretti |
| 6,630,143 B1 | 10/2003 | Lyman et al. |
| 6,682,736 B1 | 1/2004 | Hanson et al. |
| 6,692,740 B2 | 2/2004 | Sims et al. |
| 6,716,587 B2 | 4/2004 | Mosley et al. |
| 6,740,522 B2 | 5/2004 | Anderson |
| 6,849,450 B2 | 2/2005 | Langley et al. |
| 6,924,360 B2 | 8/2005 | Green et al. |
| 7,012,689 B2 | 3/2006 | Sharpe |
| 7,037,498 B2 | 5/2006 | Cohen et al. |
| 7,045,128 B2 | 5/2006 | Lyman et al. |
| 7,067,131 B2 | 6/2006 | Gudas et al. |
| 7,081,523 B2 | 7/2006 | Elliott |
| 7,084,257 B2 | 8/2006 | Deshpande et al. |
| 7,090,844 B2 | 8/2006 | Bar-Eli et al. |
| 7,109,003 B2 | 9/2006 | Hanson et al. |
| 7,132,281 B2 | 11/2006 | Hanson et al. |
| 7,135,174 B2 | 11/2006 | Corvalan et al. |
| 7,138,500 B1 | 11/2006 | Goodwin et al. |
| 7,141,653 B2 | 11/2006 | Greenfeder et al. |
| 7,144,731 B2 | 12/2006 | Zsebo et al. |
| 7,186,809 B2 | 3/2007 | Pluenneke |

(Continued)

FOREIGN PATENT DOCUMENTS

| | | |
|---|---|---|
| EP | 0546073 B1 | 9/1997 |
| WO | WO-90/04036 A1 | 4/1990 |
| WO | WO-94/02602 A1 | 2/1994 |
| WO | WO-96/33735 A1 | 10/1996 |
| WO | WO-1997/026883 | 7/1997 |
| WO | WO-1999/010494 | 3/1999 |
| WO | WO-2000/024245 | 5/2000 |
| WO | WO-2002/089832 | 11/2002 |

(Continued)

OTHER PUBLICATIONS

Allakhverdi et al., CD34+ hemopoietic progenitor cells are potent effectors of allergic inflammation, *J. Allergy Clin. Immunol.*, 123:472-8 (2009).

(Continued)

*Primary Examiner* — Daniel C Gamett
(74) *Attorney, Agent, or Firm* — Marshall, Gerstein & Borun LLP

(57) ABSTRACT

The present disclosure relates to a method for detecting T helper cell or CTL subpopulations in a subject affected by disease or disorder having an immune component. The methods are also useful for determining efficacy of a treatment of the disease or disorder by detecting skewing of the T helper cells and CTLs in a therapeutic or adverse direction.

23 Claims, 5 Drawing Sheets

(56) References Cited

U.S. PATENT DOCUMENTS

| | | | |
|---|---|---|---|
| 7,193,058 B2 | 3/2007 | Cosman et al. |
| 7,199,224 B2 | 4/2007 | Black et al. |
| 7,202,343 B2 | 4/2007 | Gudas et al. |
| 7,265,212 B2 | 9/2007 | Babcock et al. |
| 7,267,960 B2 | 9/2007 | Galibert et al. |
| 7,270,817 B2 | 9/2007 | Sims et al. |
| 7,285,269 B2 | 10/2007 | Babcock et al. |
| 7,288,251 B2 | 10/2007 | Bedian et al. |
| 7,288,253 B2 | 10/2007 | Roskos et al. |
| 7,304,144 B2 | 12/2007 | Sims et al. |
| 7,317,090 B2 | 1/2008 | Mosley et al. |
| 7,318,925 B2 | 1/2008 | Roskos et al. |
| 7,326,414 B2 | 2/2008 | Bedian et al. |
| 7,335,743 B2 | 2/2008 | Welcher et al. |
| 7,338,660 B2 | 3/2008 | Bedian et al. |
| 7,371,381 B2 | 5/2008 | Aaron et al. |
| 7,378,091 B2 | 5/2008 | Gudas et al. |
| 7,411,050 B2 | 8/2008 | Anderson |
| 7,411,057 B2 | 8/2008 | Hanson et al. |
| 7,422,742 B2 | 9/2008 | Greenfeder et al. |
| 7,423,128 B2 | 9/2008 | Gazit-Bornstein et al. |
| 7,427,669 B2 | 9/2008 | Cosman et al. |
| 7,435,796 B1 | 10/2008 | Yoshinaga |
| 7,438,910 B2 | 10/2008 | Varnum et al. |
| 7,449,555 B2 | 11/2008 | Fanslow, III et al. |
| 7,465,450 B2 | 12/2008 | Pluenneke |
| 7,498,420 B2 | 3/2009 | Michaud et al. |
| 7,521,048 B2 | 4/2009 | Gliniak et al. |
| 7,521,053 B2 | 4/2009 | Oliner |
| 7,537,762 B2 | 5/2009 | North et al. |
| 7,541,438 B2 | 6/2009 | Tamatani et al. |
| 7,563,442 B2 | 7/2009 | Bedian et al. |
| 7,566,772 B2 | 7/2009 | Green et al. |
| 7,569,387 B2 | 8/2009 | Theill et al. |
| 7,579,186 B1 | 8/2009 | Sakamoto et al. |
| 7,585,500 B2 | 9/2009 | Foltz et al. |
| 7,592,429 B2 | 9/2009 | Paszty et al. |
| 7,592,430 B2 | 9/2009 | Bedian et al. |
| 7,601,818 B2 | 10/2009 | Wild, Jr. et al. |
| 7,618,633 B2 | 11/2009 | Bedian et al. |
| 7,626,012 B2 | 12/2009 | Bedian et al. |
| 7,628,986 B2 | 12/2009 | Weber et al. |
| 7,638,606 B2 | 12/2009 | Carter et al. |
| 7,658,924 B2 | 2/2010 | Oliner et al. |
| 7,695,948 B2 | 4/2010 | Black et al. |
| 7,700,742 B2 | 4/2010 | Cohen et al. |
| 7,704,501 B2 | 4/2010 | Anderson |
| 7,705,130 B2 | 4/2010 | Rothe et al. |
| 7,709,611 B2 | 5/2010 | Li et al. |
| 7,718,776 B2 | 5/2010 | Boyle et al. |
| 7,728,110 B2 | 6/2010 | Babcook et al. |
| 7,728,113 B2 | 6/2010 | Bedian et al. |
| 7,736,644 B2 | 6/2010 | Weber et al. |
| 7,741,115 B2 | 6/2010 | Baum et al. |
| 7,767,206 B2 | 8/2010 | Tocker et al. |
| 7,767,793 B2 | 8/2010 | Sims |
| 7,786,234 B2 | 8/2010 | Dershem et al. |
| 7,786,271 B2 | 8/2010 | Sims et al. |
| 7,786,284 B2 | 8/2010 | Tocker et al. |
| 7,790,859 B2 | 9/2010 | Welcher et al. |
| 7,795,413 B2 | 9/2010 | Wild, Jr. et al. |
| 7,807,159 B2 | 10/2010 | Chin et al. |
| 7,807,795 B2 | 10/2010 | Boyle |
| 7,807,796 B2 | 10/2010 | Cosman et al. |
| 7,807,797 B2 | 10/2010 | Hanson et al. |
| 7,807,798 B2 | 10/2010 | Jakobovits et al. |
| 7,815,907 B2 | 10/2010 | Cohen et al. |
| 7,824,679 B2 | 11/2010 | Hanson et al. |
| 7,833,527 B2 | 11/2010 | Tocker et al. |
| 7,867,494 B2 | 1/2011 | Liu et al. |
| 7,868,140 B2 | 1/2011 | Siu et al. |
| 7,871,611 B2 | 1/2011 | Calzone et al. |
| 7,872,106 B2 | 1/2011 | Paszty et al. |
| 7,872,113 B2 | 1/2011 | Carter et al. |
| 7,879,323 B2 | 2/2011 | Thomason et al. |
| 7,887,799 B2 | 2/2011 | Thomason et al. |
| 7,888,482 B2 | 2/2011 | Virca et al. |
| 7,906,625 B2 | 3/2011 | Shen et al. |
| 7,915,391 B2 | 3/2011 | Ng et al. |
| 7,923,008 B2 | 4/2011 | Boyle |
| 7,932,372 B2 | 4/2011 | Pullen et al. |
| 7,932,503 B2 | 4/2011 | Parks et al. |
| 7,939,070 B2 | 5/2011 | Tocker et al. |
| 7,939,640 B2 | 5/2011 | Baum |
| 7,947,809 B2 | 5/2011 | Yan et al. |
| 7,964,193 B2 | 6/2011 | Green et al. |
| 7,982,016 B2 | 7/2011 | Comeau et al. |
| 8,101,182 B2 | 1/2012 | Dong et al. |
| 8,232,372 B2 | 7/2012 | Presta et al. |
| 8,389,291 B2 | 3/2013 | Durack et al. |
| 8,435,518 B2 | 5/2013 | Tocker et al. |
| 8,545,842 B2 | 10/2013 | Tocker et al. |
| 2001/0006789 A1 | 7/2001 | Maino et al. |
| 2003/0103978 A1 | 6/2003 | Deshpande et al. |
| 2006/0127393 A1 | 6/2006 | Li et al. |
| 2007/0196376 A1 | 8/2007 | Raeber et al. |
| 2008/0166352 A1 | 7/2008 | Siu et al. |
| 2008/0182976 A1 | 7/2008 | Elliott |
| 2008/0286284 A1 | 11/2008 | Maddon et al. |
| 2008/0292639 A1 | 11/2008 | Shen et al. |
| 2009/0041784 A1 | 2/2009 | Yan et al. |
| 2009/0155164 A1 | 6/2009 | Brasel et al. |
| 2009/0155274 A1 | 6/2009 | Wild, Jr. et al. |
| 2009/0186022 A1 | 7/2009 | Bardroff et al. |
| 2009/0191212 A1 | 7/2009 | Oliner et al. |
| 2009/0208489 A1 | 8/2009 | Veiby et al. |
| 2009/0214559 A1 | 8/2009 | Varnum et al. |
| 2009/0226447 A1 | 9/2009 | Boone et al. |
| 2009/0234106 A1 | 9/2009 | Han et al. |
| 2009/0238823 A1 | 9/2009 | Comeau et al. |
| 2009/0263383 A1 | 10/2009 | Smothers et al. |
| 2010/0040619 A1 | 2/2010 | Li et al. |
| 2010/0047253 A1 | 2/2010 | Foltz et al. |
| 2010/0098694 A1 | 4/2010 | Bedian et al. |
| 2010/0111979 A1 | 5/2010 | Weber et al. |
| 2010/0197005 A1 | 8/2010 | Belouski et al. |
| 2010/0209435 A1 | 8/2010 | Boyle et al. |
| 2010/0254975 A1 | 10/2010 | Hsu et al. |
| 2010/0255538 A1 | 10/2010 | Cohen et al. |
| 2010/0305307 A1 | 12/2010 | Jakobovits et al. |
| 2011/0014201 A1 | 1/2011 | Smith et al. |
| 2011/0027287 A1 | 2/2011 | Jackson et al. |
| 2011/0040076 A1 | 2/2011 | Wild, Jr. et al. |
| 2011/0044986 A1 | 2/2011 | Biere-Citron et al. |
| 2011/0045537 A1 | 2/2011 | Welcher et al. |
| 2011/0059063 A1 | 3/2011 | Virca et al. |
| 2011/0091455 A1 | 4/2011 | Chin et al. |
| 2011/0135657 A1 | 6/2011 | Hu et al. |
| 2011/0150888 A1 | 6/2011 | Foltz et al. |
| 2011/0165171 A1 | 7/2011 | Vicra et al. |
| 2013/0022621 A1 | 1/2013 | Liu et al. |

FOREIGN PATENT DOCUMENTS

| | | |
|---|---|---|
| WO | WO-2004/019764 | 3/2004 |
| WO | WO-2008/076321 A1 | 6/2008 |
| WO | WO-2010/065929 | 6/2010 |

OTHER PUBLICATIONS

Allakhverdi et al., Thymic stromal lymphopoietin is released by human epithelial cells in response to microbes, trauma, or inflammation and potently activates mast cells, *J. Exp. Med.*, 204:253-8 (2007).

American Thoracic S. et al., ATS/ERS recommendations for standardized procedures for the online and offline measurement of exhaled lower respiratory nitric oxide and nasal nitric oxide, *Am. J. Respir. Crit. Care Med.*, 171:912-30 (2005).

Atamas et al., Cytokine regulation of pulmonary fibrosis in scleroderma, *Cytokine Growth Factor Rev.*, 14:537-50 (2003).

Bates et al., Animal models of asthma, *Am. J. Physiol. Lung Cell Mol. Physiol.*, 297(3):L401-10 (2009).

(56) References Cited

OTHER PUBLICATIONS

Boulet et al., Asthma and increases in nonallergic bronchial responsiveness from seasonal pollen exposure, *J. Allergy Clin. Immunol.*, 71:399-406 (1983).

Bregenholtant et al., Increased intracellular Th1 cytokines in scid mice with inflammatory bowel disease, *Eur. J. Immunol.*, 28(1):379-89 (1998).

Bruggermann et al., Designer mice: the production of human antibody repertoires in transgenic animals, *Year in Immunol.*, 7:33 (1993).

Bunyavanich et al., Thymic stromal lymphopoietin (TSLP) is associated with allergic rhinitis in children with asthma, *Clin. Mol. Allergy*, 9:1 (2011).

Cockcroft et al., Prediction of airway responsiveness to allergen from skin sensitivity to allergen and airway responsiveness to histamine, *Am. Rev. Respir. Dis.*, 135:264-7 (1987).

Corren et al., Lebrikizumab treatment in adults with asthma, *N. Engl. J. Med.*, 365:1088-98 (2011).

Corrigan et al., Early production of thymic stromal lymphopoietin precedes infiltration of dendritic cells expressing its receptor in allergen-induced late phase cutaneous responses in atopic subjects, *Allergy*, 64:1014-22 (2009).

Dahlen et al.. Effect of formoterol with or without budesonide in repeated low-dose allergen challenge, *Eur. Respir. J.*, 33:747-53 (2009).

Dai et al., Long-lasting complete regression of established mouse tumors by counteracting Th2 inflammation, *J. Immunother.*, 36(4):248-57 (2013).

Davis et al., Single-dose desloratadine and montelukast and allergen-induced late airway responses, *Eur. Respir. J.*, 33:1302-8 (2009).

Defrances et al., 2006 National Hospital Discharge Survey, *National Health Statistics Reports*, Jul. 5, 30, 2008.

Diamant et al., Inhaled allergen bronchoprovocation tests, *J. Allergy Clin. Immunol.*, 132:1045-55 (2013).

Ferreira et al., Genome-wide association analysis identifies 11 risk variants associated with the asthma with hay fever phenotype, *J. Allergy Clin. Immunol.*, 133(6):1564-71 (2013).

Gauvreau et al., Effects of interleukin-13 blockade on allergen-induced airway responses in mild atopic asthma, *Am. J. Respir. Crit. Care Med.*, 183:1007-14 (2011).

Gauvreau et al., Increased Number of both airway basophils and mast cells in sputum after allergen inhalation challenge of atopic asthmatics, *Am. J. Respir. Crit. Care Med.*, 161:1473-8 (2000).

Gauvreau et al., Kinetics of allergen-induced airway eosinophilic cytokine production and airway inflammation, *Am. J. Respir. Crit. Care Med.*, 160:640-7 (1999).

Gauvreau et al., OX40L blockade and allergen-induced airway responses in subjects with mild asthma, *Clin. Exp. Allergy*, 44:29-37 (2014).

Gauvreau et al., Repeatability of allergen-induced airway inflammation, *J. Allergy Clin. Immunol.*, 104:66-71 (1999).

Gavala et al., Virus/allergen interactions in asthma, *Curr. Allergy Asthma Rep.*, 13:298-307 (2013).

Gilliet, Human dendritic cells activated by TSLP and CD40L induce proallergic cytotoxic T cells, *J. Exp. Med.*, 197:1059-67 (2003).

Green et al., Synergism between allergens and viruses and risk of hospital admission with asthma: case-control study, *BMJ*, 324:763 (2002).

Haldar et al., Mepolizumab and exacerbations of refractory eosinophilic asthma, *N. Engl. J. Med.*, 360:973-84 (2009).

Harada et al., Thymic stromal lymphopoietin gene promoter polymorphisms are associated with susceptibility to bronchial asthma, *Am. J. Respir. Cell. Mol. Biol.*, 44:787-93 (2011).

He et al., A thymic stromal lymphopoletin gene variant is associated with asthma and airway hyperresponsiveness, *J. Aller. Clin. Immunol.*, 124:222-9 (2009).

Hoogenboom et al., By-passing immunisation. Human antibodies from synthetic repertoires of germline VH gene segments rearranged in vitro, *J. Mol. Biol.*, 227:381 (1991).

Ikeda et al., The roles of IFN gamma in protection against tumor development and cancer immunoediting, *Cytokine Growth Factor Rev.*, 13:95-109 (2002).

Inman et al., Allergen-induced increase in airway responsiveness, airway eosinophilia, and bone-marrow eosinophil progenitors in mice, *Am. J. Respir. Cell. Mol. Biol.*, 21:473-9 (1999).

Inman et al., Reproducibility of allergen-induced early and late asthmatic responses, *J. Aller. Clin. Immunol.*, 95:1191-5 (1995).

Ito et al., Prognostic significance of T helper 1 and 2 and T cytotoxic 1 and 2 cells in patients with non-small cell lung cancer, *Anticancer Res.*, 25:2027-31 (2005).

Itoi et al., Relationship between diabetic macular edema and peripheral Th1/Th2 balance, *Ophthalmologica*, 222(4):249-53 (2008).

Jakobovits et al., Germ-line transmission and expression of a human-derived yeast artificial chromosome, *Nature*, 362:255-8 (1993).

Jakobovits et al., Analysis of homozygous mutant chimeric mice: deletion of the immunoglobulin heavy-chain joining region blocks B-cell development and antibody production, *Proc. Natl. Acad. Sci.* 90:2551-5 (1993).

Jones et al., Streptomyces Exploration: Competition, Volatile Communication and New Bacterial Behaviours, *Nature*, 321:522-25 (1986).

Kato et al., TLR3- and Th2 cytokine-dependent production of thymic stromal lymphopoietin in human airway epithelial cells, *J. Immunol.*, 179:1080-7 (2007).

Kelly et al., Re-evaluation of fibrogenic cytokines in lung fibrosis, *Curr. Pharma Design*, 9:39-49 (2003).

Kitajima et al., TSLP enhances the function of helper type 2 cells, *Eur. J. Immunol.*, 44(7):1862-71 (2011).

Leckie et al., Effects of an interleukin-5 blocking monoclonal antibody on eosinophils, airway hyper-responsiveness, and the late asthmatic response, *Lancet*, 356:2144-8 (2000).

Liu, Thymic stromal lymphopoietin: master switch for allergic inflammation, *J. Exp. Med.*, 203:269-73 (2006).

Lore et al., Toll-like receptor ligands modulate dendritic cells to augment cytomegalovirus- and HIV-1-specific T cell responses, *J. Immunol.*, 171:4320-28 (2003).

Ludviksson et al., Active Wegener's granulomatosis is associated with HLA-DR+ CD4+ T cells exhibiting an unbalanced Th1-type T cell cytokine pattern: reversal with IL-10, *J. Immunol.*, 160:3602-9 (1998).

Marks et al., By-passing immunization. Human antibodies from V-gene libraries displayed on phage, *J. Mol. Biol.*, 222:581-97 (1991).

Mishra et al., From bedside to bench to clinic trials: identifying new treatments for severe asthma, *Dis. Model. Mech.*, 6:877-88 (2013).

Mjosberg et al., The transcription factor GATA3 is essential for the function of human type 2 innate lymphoid cells, *Immunity*, 37:649-59 (2012).

Morrison et al., Chimeric human antibody molecules: mouse antigen-binding domains with human constant region domains, *Proc. Natl. Acad. Sci.*, 81:6851-55 (1985).

Muranski et al., Essentials of Th17 cell commitment and plasticity, *Blood*, 121:2402-14 (2013).

Nair et al. Mepolizumab for prednisone-dependent asthma with sputum eosinophilia, *N. Engl. J. Med.*, 360:985-93 (2009).

Nolte et al., Dose-dependent anti-inflammatory effect of inhaled mometasone furoate/formoterol in subjects with asthma, *Respir. Med.*, 107:656-64 (2013).

O'Byrne et al., Late asthmatic responses, *Am. Rev. Respir. Dis.*, 136:740-51 (1987).

Pandey, Cloning of a receptor subunit required for signaling by thymic stromal lymphopoietin, *Nat. Immunol.*, 1:59-64 (2000).

Parameswaran et al., Role for cysteinyl leukotrienes in allergen-induced change in circulating dendritic cell number of asthma, *J. Aller. Clin. Immunol.*, 114:73-9 (2004).

Park, Antiplatelet activity of obovatol, a biphenolic component of Magnolia Obovata, in rat arterial thrombosis and rabbit platelet aggregation, *J. Exp. Med.*, 192:659-69 (2000).

Partridge, *Eur. Resp. Rev.*, 16:67-72, 2007.

Pizzichini et al. Indices of airway inflammation in induced sputum: reproducibility and validity of cell and fluid-phase measurements, *Am. J. Respir. Crit. Care Med.*, 154:308-17 (1996).

(56) References Cited

OTHER PUBLICATIONS

Proposed International Nonproprietary Names: List 102 (WHO Drug Information, 23(4) World Health Organization (2009).
Proposed International Nonproprietary Names: List 105 (WHO Drug Information, 25(2) World Health Organization (2011).
Reche et al., Human thymic stromal lymphopoietin preferentially stimulates myeloid cells, *J. Immunol*, 167:336-43 (2001).
Recommended International Nonproprietary Names: List 67 (WHO Drug Information, 26(1) World Health Organization (2012).
Recommended International Nonproprietary Names: List 69 (WHO Drug Information 27(1) World Health Organization (2013).
Recommended International Nonproprietary Names: List 70 (WHO Drug Information, 27(3) World Health Organization (2013).
Riechmann et al., Reshaping human antibodies for therapy, *Nature*, 332:323-27 (1988).
Sears et al., Atopy in childhood. I. Gender and allergen related risks for development of hay fever and asthma, *Clin. Exp. Allergy*, 23:941-8 (1993).
Sfanos et. al., Phenotypic analysis of prostate-infiltrating lymphocytes reveals TH17 and Treg skewing, *Clin. Can. Res*., 14:3254-61 (2008).
Singleton et al., Dictionary of Microbiology and Molecular Biology, 2nd Ed. (1994).
Soumelis et al., Human epithelial cells trigger dendritic cell mediated allergic inflammation by producing TSLP, *Nat. Immunol.*, 3:673-80 (2002).
The Cambridge Dictionary of Science and Technology, Walker Ed., (1988).
The Glossary of Genetics, 5th Ed., R. Rieger et al. (Eds.), Springer Verlag (1991).
Tojo et al., Comparison of Interleukin-17-Producing Cells in Different Clinical Types of Alopecia Areata, *Dermatol.*, 227(1): 78-82 (2013).
Toldi et al., Peripheral Th1/Th2/Th17/regulatory T-cell balance in asthmatic pregnancy, *Internat. Immunol.*, 23(11): 669-77 ( 2011).
Verhoeyen et al., Reshaping human antibodies: grafting an antilysozyme activity, *Science*, 239:1534-36 (1988).
Wang et. al., PD1 blockade reverses the suppression of melanoma antigen-specific CTL by CD4+ CD25(Hi) regulatory T cells, *Int. Imm.*, 21:1065-77 (2009).
Warrington et al., Characterisation of the immune response to type I collagen in scleroderma, *Arthritis Res Ther.*, 8(4):R136 (2006).
Wenzel et al, Dupilumab in persistent asthma with elevated eosinophil levels, *N. Engl. J. Med.*, 368:2455-66 (2013).
Ying et al., Thymic stromal lymphopoietin expression is increased in asthmatic airways and correlates with expression of Th2-attracting chemokines and disease severity, *J. Immunol*, 174:8183-90 (2005).
Ying et al., Expression and cellular provenance of thymic stromal lymphopoietin and chemokines in patients with severe asthma and chronic obstructive pulmonary disease, *J. Immunol.*, 181:2790-8 (2008).
Zhou et al. Thymic stromal lymphopoietin as a key initiator of allergic airway inflammation in mice, *Nat. Immunol.*, 6:1047-53 (2005).
Zhu et al., Differentiation of effector CD4 T cell populations (*), *Annu Rev Immunol.*, 28: 445-89 (2010).
International Search Report and Written Opinion of the International Search Authority, European Patent Office, PCT/US2015/030940, dated Nov. 19, 2015.
International Preliminary Report on Patentability, European Patent Office, PCT/US2015/030940, dated Nov. 22, 2016.

Figure 2

Treatment Differences in Allergen-Induced Airway Responses

| Response | Day | Measure Unit | Placebo | AMG 157 | Treatment Difference Estimate | 95% Confidence Intervals | P-values |
|---|---|---|---|---|---|---|---|
| LAR | 42 | Maximum % fall $FEV_1$ | −22.53 | −14.88 | 7.65 | (−1.30, 16.60) | 0.09 |
| | | %$FEV_1$-time $AUC_{3-7h}$ | 12.75 | 8.40 | −4.35 | (−9.80, 1.10) | 0.11 |
| | | Minimum $FEV_1$ (L) | 2.60 | 3.01 | 0.41* | (0.12, 0.70) | 0.01 |
| | | $FEV_1$-time $AUC_{3-7h}$ | 2.94 | 3.19 | 0.24* | (0.04, 0.45) | 0.02 |
| | 84 | Maximum % fall $FEV_1$ | −21.58 | −11.67 | 9.91* | (1.59, 18.23) | 0.02 |
| | | %$FEV_1$-time $AUC_{3-7h}$ | 12.34 | 7.68 | −4.66 | (−9.71, 0.39) | 0.07 |
| | | Minimum $FEV_1$ (L) | 2.63 | 3.05 | 0.42* | (0.11, 0.72) | 0.01 |
| | | $FEV_1$-time $AUC_{3-7h}$ | 2.96 | 3.15 | 0.18 | (−0.07, 0.44) | 0.15 |
| EAR | 42 | Maximum % fall $FEV_1$ | −31.83 | −23.26 | 8.57* | (0.01, 17.13) | 0.05 |
| | | %$FEV_1$-time $AUC_{0-2h}$ | 17.73 | 11.65 | −6.08* | (−11.56, −0.60) | 0.03 |
| | | Minimum $FEV_1$ (L) | 2.30 | 2.64 | 0.33* | (−0.01, 0.68) | 0.05 |
| | | $FEV_1$-time $AUC_{0-2h}$ | 2.77 | 3.05 | 0.28* | (0.03, 0.53) | 0.03 |
| | 84 | Maximum % fall $FEV_1$ | −32.94 | −22.67 | 10.27 | (−0.46, 21.00) | 0.06 |
| | | %$FEV_1$-time $AUC_{0-2h}$ | 19.53 | 12.10 | −7.44* | (−14.22, −0.66) | 0.03 |
| | | Minimum $FEV_1$ (L) | 2.25 | 2.65 | 0.39 | (−0.06, 0.84) | 0.08 |
| | | $FEV_1$-time $AUC_{0-2h}$ | 2.69 | 3.02 | 0.33 | (−0.01, 0.66) | 0.06 |
| Methacholine $PC_{20}$ | 43-41 | Log2 PC20 delta (mg/ml) | −0.90 | −0.14 | 0.76 | (−0.04, 1.56) | 0.06 |
| | 85-83 | Log2 PC20 delta (mg/ml) | −0.69 | −0.19 | 0.49 | (−0.30, 1.28) | 0.21 |

ASSAY FOR DETECTING TH1 AND TH2 CELL POPULATIONS

FIELD OF THE INVENTION

The present disclosure relates to a method for detecting T helper (Th) cell and polyfunctional cytotoxic T-cells (CTL) subpopulations in in a subject affected by disease or disorder having an immune component. The methods are also useful for determining efficacy of a treatment of the disease or disorder by detecting skewing of the T helper or CTL cells in a therapeutic or adverse direction.

BACKGROUND OF THE INVENTION

T-cell subsets include helper T-cells (CD4+) and cytotoxic T-cells (CD8+ CTL). CD4+ helper T cells can generally be broken down into several different subtypes. Commonly divided populations include T helper 1 (Th1) and T helper 2 (Th2) cells which have been found to play distinct roles in mediating immune-related diseases and disorders. Th1 and Th2 cells can be distinguished based on their cytokine expression profile. Th1 cells typically express interferon-gamma (IFN-g, IFN-γ), lymphotoxin, (LT), and can also secrete interleukin-2 (IL-2) and tumor necrosis factor-alpha (TNF-a, TNF-α) (Zhu et al., Annu Rev Immunol. 28: 445-489, 2010). Th2 cells are characterized by production of IL-4, IL-5 and IL-13, and do not secrete IFN-γ or lymphotoxin. Some Th2 cells have been found to produce TNF-α and IL-9 (Zhu, supra). Th17 cells have also recently been determined to be a different subset of T helper cells. Th17 cells secrete IL-17A, IL-17F, and IL-22 cytokines, and can also produce IL-21. The dysregulation of the ratio of Th1 to Th2 cells, as well as Th17 cells, has been associated with certain disease states, including autoimmune diseases, allergic reactions and cancers. Two additional CD4+ T-cell subsets that can be identified by cytokine production include Treg (IL-10) and follicular helper T cells (Tfh) (IL-21).

Polyfunctional, CD8+ CTL are important effector cells that provide protection from intracellular pathogens and tumors where polyfunctionality is defined as production of multiple cytokines including (e.g. IFN-g, TNF-a and/or IL-2). In cancer subjects these polyfunctional T-cell responses have been shown to be repressed. Several new treatments (e.g. anti-CTLA4, anti-PD1) have been shown reverse functional suppression of CTL and combination with TVEC (talimogene laherparepvec) holds further promise for increasing the number of functional, activated CTL that can contribute to meaningful anti-tumor responses. Additional T cell subsets include natural killer T cells (NKT) and gamma delta T cells (gdT).

Determining levels of T cells in vivo and determining the levels of cytokines produced by these cells can be difficult. Recent advances in laboratory techniques have provided several methods for determining T helper subtypes and cytokine levels, including ELISA, ELISPOT, and flow cytometry assays, including intracellular cytokine staining assays. Despite the advancement in methodology, it is still difficult to identify particular T cell subtypes and their cytokine profiles in a patient with a disease or disorder because the levels of these particular cell types and cytokines in a given patient sample can be low to undetectable.

A common technique to identify and separate one cell type from another is flow cytometry using labeled dyes, e.g., in a fluorescence activated cells sorter (FACS). Methods of carrying out flow cytometry are discussed, for example, in U.S. Pat. No. 8,389,291, U.S. Pat. No. 7,932,503, U.S. Pat. No. 7,012,689, and U.S. Pat. No. 6,287,791.

In addition to cytokines, combinations of cell surface markers can also be used to classify T-cells by subset (e.g. Th2 cells express CRTH2) or activation status (e.g. activated CTL express HLA-DR) by FACS.

Previous studies have undertaken experiments to analyze T helper cell profiles in response to stimuli. International Patent Publication WO 1997/026883 describes intracellular cytokine staining for IL-2 only on PBMC stimulated in vitro with PMA/ionomycin with or without Ribavirin®. The results provided describe a putative pharmacological effect based on in vitro data.

U.S. Pat. No. 6,039,969 describes animal model data demonstrating that a class of compounds including the drug imiquimod can skew the immune response away from Th2, based primarily on secreted cytokine results. Human clinical data and intracellular cytokine staining were not disclosed.

U.S. Patent Publication 2001/0006789 describes a method used to identify antigen specific T-cells. Measurement of pharmacological effects on antigen specific T-cells is not demonstrated.

International Patent Publication WO 2000/024245 describes a method for targeting NFATp and/or NFAT4 to modulate Th2 cells. WO 2002/089832 relates to a combination of cytokine+SDF-1a to skew the Th1/Th2 ratio. In vitro data, including intracellular cytokine staining specific for IFN-g and IL-4, using cultured cord blood T-cells are presented. Human clinical data demonstration is not included.

Lore et al. (J Immunol 171:4320-28, 2003) describes analysis of CMV- and HIV-specific CD4+ and CD8+ T cells using a method in which levels of the Th1-specific cytokines IFN-g, TNF-a and IL-2 are measured in a single sample by flow cytometric analysis. The Th1 cytokines are detected using cytokine-specific antibodies, each of which is labeled with the same fluorophore. This method does not determine the ratio of Th1 to Th2 cells.

Ludviksson et. al. (J Immunol 160:3602-3609, 1998) describes association of Wegener's Granulomatosis with HLA-DR+CD4+ cells exhibiting unbalanced Th1 cell cytokine pattern and reversal with IL-10. Wang et. al. (Int Imm 21:1065-1077, 2009) demonstrate that PD1 blockade reverses functional suppression of CTL in melanoma setting. Sfanos et. al. (Clin Cancer Res 14:3254-3261, 2008) demonstrate skewing of tumor infiltrating lymphocytes to Th17 and Treg subsets in prostate cancer.

The present disclosure is directed to methods for identifying and differentiating a population of T helper or CTL cells in a subject having a disease or disorder with an immune component. The present technique can be carried out before and after treatment with a therapeutic agent to improve treatment regimens for patients receiving therapy.

SUMMARY OF THE INVENTION

The present disclosure provides a method for measuring changes in T cell subset populations in a subject having a disease or disorder or subsequent to a treatment regimen. The method is useful to determine efficacy of a treatment regimen and assist in designing an optimal treatment regimen for a patient.

The present disclosure provides a method for detecting a ratio of T helper 2 (Th2) and T helper 1 (Th1) cells in a sample from a patient comprising measuring levels of Th2-specific and Th1-specific cytokines, the method comprising a) contacting the sample with i) two or more specific binding agents that bind two or more Th2 cytokines, wherein the two or more specific binding agents for the Th2-specific cytokines are labeled with a first fluorophore; and ii) at least one specific binding agent that binds a Th1 cytokine, wherein the specific binding agent for the Th1 cytokine is labeled with a second fluorophore that is different from the first fluorophore; b) measuring levels of the first and second fluorophores in the sample and designating the cell as a Th1 or Th2 cell based on the level of Th1-specific and Th2-specific fluorophore detected; and c) determining the ratio of Th2 to Th1 cells in a sample.

In various embodiments, the method further comprises determining the ratio of Th1, Th2 and Th17 cells in the sample, comprising a) contacting the sample with iii) at least one specific binding agent that binds a Th17 cytokine, wherein the specific binding agent for the Th17 cytokine is labeled with a second fluorophore that is different from the first fluorophore or labeled with a third fluorophore; b) measuring levels of the first and second (and/or third) fluorophores in the sample and designating the cell as a Th1, Th2 or Th17 cell based on the level of Th1-specific, Th2-specific or Th17-specific fluorophore detected; and c) determining the ratio of Th1 to Th2 to Th17 cells in a sample.

In various embodiments, the disclosure provides a method for detecting a ratio of T helper 1 (Th1) and T helper 17 (Th17) cells in a sample from a patient comprising measuring levels of Th1-specific and Th17-specific cytokines, the method comprising: a) contacting the sample with i) two or more specific binding agents that bind two or more Th17 cytokines, wherein the two or more specific binding agents for the Th17-specific cytokines are labeled with a first fluorophore; and ii) at least one specific binding agent that binds a Th1 cytokine, wherein the specific binding agent for the Th1 cytokine is labeled with a second fluorophore that is different from the first fluorophore; b) measuring levels of the first and second fluorophores in the sample and designating the cell as a Th1 or Th17 cell based on the level of Th1-specific and Th17-specific fluorophore detected; and c) determining the ratio of Th1 to Th17 cells in a sample.

In various embodiments, the disclosure provides a method for detecting a ratio of T helper 2 (Th2) and T helper 17 (Th17) cells in a sample from a patient comprising measuring levels of Th2-specific and Th17-specific cytokines, the method comprising: a) contacting the sample with i) two or more specific binding agents that bind two or more Th2 cytokines, wherein the two or more specific binding agents for the Th2-specific cytokines are labeled with a first fluorophore; and ii) at least one specific binding agent that binds a Th17 cytokine, wherein the specific binding agent for the Th17 cytokine is labeled with a second fluorophore that is different from the first fluorophore; b) measuring levels of the first and second fluorophores in the sample and designating the cell as a Th2 or Th17 cell based on the level of Th2-specific and Th17-specific fluorophore detected; and c) determining the ratio of Th2 to Th17 cells in a sample.

In certain embodiments, it is also contemplated that the ratio of Th1 to Th2 cells is calculated using the present method, and this ratio used to determine treatment efficacy and potential change in treatment regimen for a patient. Similarly, for the methods described herein, it is specifically contemplated that the converse ratio (e.g., Th17/Th1, Th17/Th2 or any combination ratio for Th1, Th2 and Th17) may be determined and a treatment decision made also based on the ratio of cells determined.

In various embodiments, the Th2 cytokines are selected from the group consisting of IL-4, IL-5 and IL-13. In various embodiments, the Th1 cytokines are selected from the group consisting of interferon gamma (IFN-g), tumor necrosis factor alpha (TNF-a) and IL-2.

In various embodiments, the Th17 cytokines are selected from the group consisting of IL-17A, IL-17F, IFN-g and IL-22.

In various embodiments, the specific binding agent is an antibody specific for a Th1-specific, Th2-specific or Th17-specific cytokine.

In various embodiments, the method further comprises a step of administering a therapeutic agent, altering a dose regimen of a therapeutic agent or maintaining a dose regimen of a therapeutic agent in view of the ratio of T cell subsets detected by the method, wherein detection of a particular ratio indicates the treatment regimen to be administered.

In various embodiments, the patient is suffering from a disease or disorder selected from the group consisting of asthma, allergic rhinosinusitis, allergic conjunctivitis, atopic dermatitis, fibrotic disorders, Systemic Lupus Erythematosus (SLE), multiple sclerosis and cancers. Additional disorders contemplated in the present methods are discussed in greater detail in the Detailed Description.

In various embodiments, the sample is obtained before and/or after treatment with a therapeutic agent. In certain embodiments, the sample is whole blood, peripheral blood mononuclear cells, cerebrospinal fluid, bronchioalveolar lavage, nasal lavage, induced sputum or a biopsy from the patient.

In various embodiments, the therapeutic agent is an anti-TSLP antibody.

In various embodiments, the first fluorophore is phycoerythrin (PE) and the second fluorophore is fluorescein isothiocyanate (FITC). Additional fluorophores contemplated for use in the method include, but are not limited to, Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, BODIPY FL, BODIPY 630/650, Cy2, Cy3, Cy3B, Cy3.5, Cy5, Cy5.5, Cy7, ECD, FITC, FluorX®, Cascade® Blue, Pacific Blue®, Pacific Green®, Pacific Orange®, eFluor® 450, eFluor® 605NC, eFluor® 625NC, eFluor® 650NC, eFluor® 660, eFluor® 710, Brilliant Violet™ (BV) fluorophores BV421, BV510, BV570, BV 605, BV650, BD Horizon™ V450, BD Horizon™ V500, Texas Red, rhodamine, cyanine, phycoerythrin (PE), phycocyanin, allophycocyanin (APC), o-phthaldehyde, fluorescamine, Oregon Green® 488, PE-APC, PE-Cy5, PerCP, PE-TR, rhodamine green and rhodol green, and tandem dyes thereof.

In one embodiment the cytokines are contacted with the specific binding agent intracellularly. In certain embodiments, the cytokines are contacted with the specific binding agents extracellularly. In certain embodiments, the cytokines are secreted from the cells in vitro or in are detectable in fluid samples.

In various embodiments, the disclosure provides a method for identifying a sub-population of asthma patients responsive to treatment with a therapeutic agent comprising measuring the baseline ratio of T helper 2 (Th2) and T helper 1 (Th1) cells in a patient sample or changes in the ratio after administration of the therapeutic agent, the method comprising: a) contacting the sample with i) two or more specific binding agents that bind two or more Th2-specific cytokines, wherein the two or more specific binding agents for the Th2-specific cytokines are labeled with a first fluorophore;

and ii) at least one specific binding agent that binds a Th1-specific cytokine, wherein the specific binding agent for the Th1-specific cytokine is labeled with a second fluorophore that is different from the first fluorophore; b) measuring levels of the first and second fluorophores in the sample and designating the cell as a Th1 or Th2 cell based on the level of Th2-specific and Th1-specific fluorophore detected; c) determining the ratio of Th2 to Th1 cells in a sample based on the level of Th2-specific cytokine and Th1-specific cytokine detected, wherein the patient is identified as responsive to the therapeutic agent if the ratio of Th2 cells/Th1 cells decreases; and d) altering treatment with the therapeutic agent if the patient is determined to be non-responsive to the therapeutic agent or maintaining the dose of therapeutic agent if the patient is determined to be responsive to treatment with the therapeutic agent. In various embodiments, the ratio of Th17 cells to Th1 and Th2 cells in the asthma patient is measured as described herein.

In various embodiments, the therapeutic agent is administered for one week, two weeks, three weeks, four weeks, six weeks, two months, three months or more prior to obtaining the sample. Additional dosing regimens contemplated by the method are discussed in greater detail in the Detailed Description.

In various embodiments, the therapeutic agent is an anti-TSLP antibody or anti-TSLP receptor antibody.

In various embodiments, the asthma patient has atopic asthma, including mild, moderate, or severe asthma. In certain embodiments, the Th2/Th1 ratio in an asthma patient is skewed toward the Th2 phenotype and this skewing could identify the patient as a candidate for treatment with a therapeutic agent that targets the Th2 pathway. In various embodiments, the patient may be a candidate for Th2 targeted therapy if the ratio of Th2/Th1 cells is approximately 0.2 or higher.

In one embodiment, the asthma patient is identified as responsive to treatment if the ratio of Th2/Th1 cells decreases by 20%, 30%, 40%, 50%, 60% or more. It is contemplated that the degree of responsiveness is compared to a baseline value obtained before or at certain points during treatment. In one embodiment, a Th2/Th1 ratio at which the patient is identified as responsive to treatment is approximately 0.1 or below.

In various embodiments, the disclosure provides a method of altering the dose regimen of an anti-TSLP agent in treating an immune disorder comprising determining the ratio of Th2/Th1 and/or Th17 cells in a sample using the method described herein and altering the dose of anti-TSLP antibody if the ratio of Th2/Th1 and/or Th17 cells changes during treatment, wherein the dose of therapeutic is increased if the ratio of Th2/Th1 cells is stable or increases indicating skewing towards Th2 profile (i.e., increasing the proportion of Th2 cells and/or decreasing the proportion of Th1 cells); and wherein the dose of therapeutic is decreased if the ratio of Th2/Th1 cells decreases indicating reduction in Th2 profile (i.e., decreasing the proportion of Th2 cells and/or increasing the proportion of Th1 cells).

In various embodiments, the immune disorder treated by an anti-TSLP or anti-TSLP receptor agent is an atopic disease or disorder. Examples of atopic diseases and disorders include, but are not limited to, asthma, allergic rhinosinusitis, allergic conjunctivitis and atopic dermatitis. In certain embodiments, the immune disorder is a fibrotic disorder.

In various embodiments, contemplated herein is a method of altering the dose regimen of an asthma therapeutic comprising determining the ratio of Th2/Th1 and/or Th17 cells in a sample using a method described herein and altering the dose of asthma therapeutic if the ratio of Th2/Th1 and/or Th17 cells changes during treatment, wherein the dose of therapeutic is increased if the ratio of Th2/Th1 cells is stable or increases indicating skewing towards Th2 profile; and wherein the dose of therapeutic is decreased if the ratio of Th2/Th1 cells decreases indicating reduction in Th2 profile.

In certain embodiments, if a high proportion of Th17 cells is detected, the method further comprises administering a therapeutic agent that inhibits IL-17 activity or the IL-17 pathway.

Also contemplated are methods of detecting CD8+ CTLs. The present disclosure provides a method for detecting a subset of CTL, such as polyfunctional CTLs, the method comprising a) contacting the sample with one or more specific binding agents that bind one or more polyfunctional CTL cytokines, wherein the one or more specific binding agents for the polyfunctional CTL cytokines are labeled with a first fluorophore and/or second fluorophore and/or third fluorophore; b) measuring levels of the first and second and/or third fluorophores in the sample and designating the cell as a polyfunctional CTL cell based on the level of specific fluorophore detected; and c) determining the ratio of polyfunctional CTL to other T cells, e.g., Th, Treg, NKT or gdT, in a sample.

In various embodiments, polyfunctional CTL cytokines are selected from the group consisting of IFN-g, IL-17, TNF-a and IL-2.

In various embodiments, cell surface markers are used for identification of T cell subpopulations. Exemplary cell surface markers include, but are not limited to, ST2, CRTH2, and CCR4 for Th2 cells, CXCR3 for Th1 cells, and/or CCR6 for Th17 cells. T cell subpopulations are also distinguished based on biomarkers indicative of activation state, including PD1, CTLA4, CD40L, ICOS, OX40, 41BB, TIM-3, GITR, HLA-DR and Ki67 of Th1, Th2, and Th17 cells.

In addition to the foregoing, the invention includes, as an additional aspect, all embodiments of the invention narrower in scope in any way than the variations defined by specific paragraphs above. For example, certain aspects of the invention that are described as a genus, and it should be understood that every member of a genus is, individually, an aspect of the invention. Also, aspects described as a genus or selecting a member of a genus, should be understood to embrace combinations of two or more members of the genus. Although the applicant(s) invented the full scope of the invention described herein, the applicants do not intend to patent subject matter described in the prior art work of others. Therefore, in the event that statutory prior art within the scope of a paragraph is brought to the attention of the applicant(s) by a Patent Office or other entity or individual, the applicant(s) reserve the right to exercise amendment rights under applicable patent laws to redefine the subject matter of such a paragraph to specifically exclude such statutory prior art or obvious variations of statutory prior art from the scope of such a paragraph. Variations of the invention defined by such amended paragraphs also are intended as aspects of the invention.

BRIEF DESCRIPTION OF THE DRAWINGS

FIG. 2 shows the treatment difference estimate (AMG 157 minus placebo) in allergen induced airway responses. Mean estimate was based on ANCOVA. AUC denotes area under the curve; EAR denotes early asthmatic response, FEV$_1$ denotes forced expiratory volume in 1 second; FEV$_1$-time AUC denotes denotes area under the curve of the time-adjusted FEV$_1$; % FEV$_1$-time AUC denotes area under the curve of the time-adjusted area under the percent fall curve in FEV$_1$; LAR denotes late asthmatic response; maximum % fall in FEV$_1$ denotes maximum percent fall in FEV (%); Methacholine PC20 denotes the provocative concentration of methacholine causing a 20% fall in FEV$_1$. *P≤0.05.

DETAILED DESCRIPTION

Figure 1:
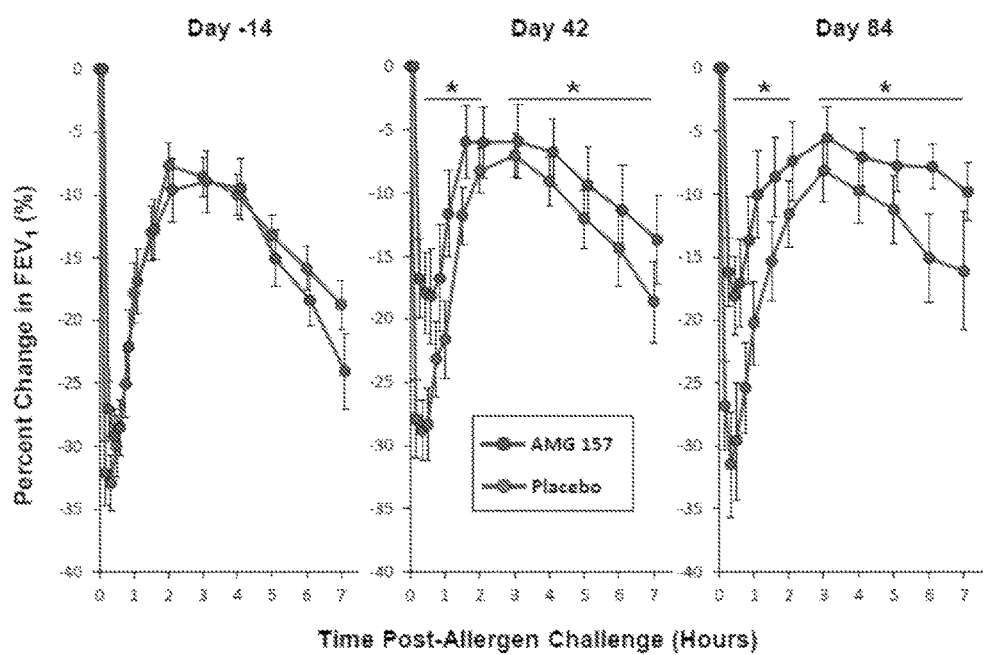
FIG. 1 illustrates the allergen-induced percent fall in $FEV_1$. Percent $FEV_1$-time curve at screening, day 42 and day 84 are presented Data are shown as mean±SEM. As compared to placebo, AMG 157 treatment significantly attenuated the late allergen-induced fall in FEV1 at days 42 and 84, and attenuated the early allergen-induced fall in FEV$_1$ at days 42 and 84. FEV$_1$ denotes forced expiratory volume in 1 second, * denotes p<0.05 AMG 157 compared to placebo.

Th2 cells are strongly implicated as contributors to establishment and progression of allergic asthma. In the clinical trial setting understanding if blocking a therapeutic target leads to changes in the Th2 cells or the Th2/Th1 ratio may be a useful exploratory objective. Moreover, the relative proportion of polarized helper T cells at baseline may help to match patients with optimal treatments. Similarly, in the cancer setting levels of Th subsets (in particular Th1, Th17 and Treg) and functionality of CTL may be useful metrics for identifying and optimizing treatment regimens. The present disclosure describes an assay to measure the change in T helper cells and CTLs developed using broad stimulation with PMA and ionomycin followed by intracellular cytokine staining to analyze the Th cytokine responses. Upon comparing a combined method of Th2 cytokine staining using IL-4, IL-5, and IL-13 together with an alternate method staining each cytokine separately, a combined method to improve the detection of Th2 cells was developed.

Definitions

Unless otherwise stated, the following terms used in this application, including the specification and claims, have the definitions given below.

As used in the specification and the appended claims, the indefinite articles "a" and "an" and the definite article "the" include plural as well as singular referents unless the context clearly dictates otherwise.

Unless otherwise defined, all technical and scientific terms used herein have the same meaning as commonly understood by one of ordinary skill in the art to which the present disclosure belongs. The following references provide one of skill with a general definition of many of the terms used in this disclosure include, but are not limited to: Singleton et al., DICTIONARY OF MICROBIOLOGY AND MOLECULAR BIOLOGY (2d Ed. 1994); THE CAMBRIDGE DICTIONARY OF SCIENCE AND TECHNOLOGY (Walker Ed., 1988); THE GLOSSARY OF GENETICS, 5th Ed., R. Rieger et al. (Eds.), Springer Verlag (1991); and Hale & Marham, THE HARPER COLLINS DICTIONARY OF BIOLOGY (1991).

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, or 0.05% of a given value or range. Whenever the term "about" or "approximately" precedes the first numerical value in a series of two or more numerical values, it is understood that the term "about" or "approximately" applies to each one of the numerical values in that series.

The term "cytokine" as used herein refers to one or more small (5-20 kD) proteins released by cells that have a specific effect on interactions and communications between cells or on the behavior of cells, such as immune cell proliferation and differentiation. Functions of cytokines in the immune system include, promoting influx of circulating leukocytes and lymphocytes into the site of immunological encounter; stimulating the development and proliferation of B cells, T cells, peripheral blood mononuclear cells (PBMCs) and other immune cells; and providing antimicrobial activity. Exemplary immune cytokines, include but are not limited to, IL-1, IL-2, IL-3, IL-4, IL-5, IL-6, IL-7, IL-9, IL-10, IL-12, IL-13, IL-15, IL17A, IL-17F, IL-18, IL-21, IL-22, interferon (including IFN alpha, beta, and gamma), tumor necrosis factor (including TNF alpha, beta), transforming growth factor (including TGF alpha, beta), granulocyte colony stimulating factor (GCSF), granulocyte macrophage colony stimulating factor (GMCSF) and thymic stromal lymphopoietin (TSLP).

A "T helper (Th) 1 cytokine" or "Th1-specific cytokine" refers to cytokines that are expressed (intracellularly and/or secreted) by Th1 T cells, and include IFN-g, TNF-a, IL-12 and in some populations, IL-2. A "Th2 cytokine" or "Th2-specific cytokine" refers to cytokines that are expressed (intracellularly and/or secreted) by Th2 T cells, including IL-4, IL-5, IL-13, IL-10, and, in certain populations IL-2. A "Th17 cytokine" or "Th17-specific cytokine" refers to cytokines that are expressed (intracellularly and/or secreted) by Th17 T cells, including IL-17A, IL-17F, IL-22 and IL-21. Certain populations of Th17 cells express IFN-g and/or IL-2 in addition to the Th17 cytokines listed herein. A polyfunctional CTL cytokine includes IFN-g, TNF-a, IL-2 and IL-17.

The term "fluorophore" refers to a small molecule dye or protein that accepts light energy at a given wavelength (excitation) and re-emits it at a longer wavelength (emission). In the present methods, fluorophores are attached to a specific binding agent, such as an antibody or enzyme substrate, and in certain embodiments detected by passing the labeled substance through a laser that causes excitation of the dye. Exemplary fluorophores useful in the present methods, include but are not limited to, Alexa Fluor® 350, Alexa Fluor® 405, Alexa Fluor® 430, Alexa Fluor® 488, Alexa Fluor® 514, Alexa Fluor® 532, Alexa Fluor® 546, Alexa Fluor® 555, Alexa Fluor® 568, Alexa Fluor® 594, Alexa Fluor® 610, Alexa Fluor® 633, Alexa Fluor® 635, Alexa Fluor® 647, Alexa Fluor® 660, Alexa Fluor® 680, Alexa Fluor® 700, BODIPY FL, BODIPY 630/650, Cy2, Cy3, Cy3B, Cy3.5, Cy5, Cy5.5, Cy7, ECD, FITC, FluorX®, Cascade® Blue, Pacific Blue®, Pacific Green®, Pacific Orange®, eFluor® 450, eFluor® 605NC, eFluor® 625NC, eFluor® 650NC, eFluor® 660, eFluor® 710, Brilliant Violet™ (BV) fluorophores BV421, BV510, BV570, BV 605, BV650, BD Horizon™ V450, BD Horizon™ V500, Texas Red, rhodamine, cyanine, phycoerythrin (PE), phycocyanin, allophycocyanin (APC), o-phthaldehyde, fluorescamine, Oregon Green® 488, PE-APC, PE-Cy5, PerCP, PE-TR, rhodamine green and rhodol green, and tandem dyes thereof.

The terms "first fluorophore" and "second fluorophore" refer to fluorophores that are useful in the method of the disclosure and are used to designate use of fluorophores that emit at different wavelengths and do not overlap in the method. For example, a "first fluorophore" refers to one or more fluorophores that are used to label one or more specific binding agents in the method and emit light at a first wavelength, and includes use of two different fluorophores that have overlapping spectral emission profiles within a first wavelength range. A "second fluorophore" refers to one or more fluorophore used in the method in which the wavelength emission of the fluorophore(s) does not overlap with the emission wavelength of the first fluorophore(s). It is also possible to carry out the method using a "third fluorophore" or further subsequent fluorophore, which includes one or more dyes that emits light at a third wavelength, or common range of wavelengths, but does not overlap spectrally with either the first fluoophore or the second fluorophore. Examples of fluorophores with overlapping spectral profiles include FITC and Alexa Fluor 488; APC, eFluor® 660 and Alexa Fluor® 647; PE and PE-Cy5; Alexa Fluor® 555 and Cy3; Alexa Fluor® 647 and Cy5; and others determined to be in overlapping emissions spectra. One of skill can determine whether fluorophores have overlapping spectra using commonly available resources that describe the emission spectra of fluorophores.

The term "specifically binds" is "antigen specific", is "specific for", "selective binding agent", "specific binding agent", "antigen target" or is "immunoreactive" with an antigen refers to an antibody or polypeptide that binds an target antigen with greater affinity than other antigens of similar sequence. It is contemplated herein that the agent specifically binds target proteins useful in identifying immune cell types, for example, a surface antigen (e.g., T cell receptor, CD3), a cytokine (e.g., TSLP, IL-4, IL-5, IL-13, IL-17, IFN-g, TNF-a) and the like.

The term "antibody" is used in the broadest sense and includes fully assembled antibodies, tetrameric antibodies, monoclonal antibodies, polyclonal antibodies, multispecific antibodies (e.g., bispecific antibodies), antibody fragments that can bind an antigen (e.g., Fab', F'(ab)2, Fv, single chain antibodies, diabodies), and recombinant peptides comprising the forgoing as long as they exhibit the desired biological activity. An "immunoglobulin" or "tetrameric antibody" is a tetrameric glycoprotein that consists of two heavy chains and two light chains, each comprising a variable region and a constant region. Antigen-binding portions may be produced by recombinant DNA techniques or by enzymatic or chemical cleavage of intact antibodies. Antibody fragments or antigen-binding portions include, inter alia, Fab, Fab', F(ab')2, Fv, domain antibody (dAb), complementarity determining region (CDR) fragments, CDR-grafted antibodies, single-chain antibodies (scFv), single chain antibody fragments, chimeric antibodies, diabodies, triabodies, tetrabodies, minibody, linear antibody; chelating recombinant antibody, a tribody or bibody, an intrabody, a nanobody, a small modular immunopharmaceutical (SMIP), an antigen-binding-domain immunoglobulin fusion protein, a camelized antibody, a VHH containing antibody, or a variant or a derivative thereof, and polypeptides that contain at least a portion of an immunoglobulin that is sufficient to confer specific antigen binding to the polypeptide, such as one, two, three, four, five or six CDR sequences, as long as the antibody retains the desired biological activity.

"Monoclonal antibody" refers to an antibody obtained from a population of substantially homogeneous antibodies, i.e., the individual antibodies comprising the population are identical except for possible naturally occurring mutations that may be present in minor amounts.

The term "sample" or "biological sample" refers to a specimen obtained from a subject for use in the present methods, and includes urine, whole blood, plasma, serum, saliva, tissue biopsies, cerebrospinal fluid, peripheral blood mononuclear cells with in vitro stimulation, peripheral blood mononuclear cells without in vitro stimulation, gut lymphoid tissues with in vitro stimulation, gut lymphoid tissues without in vitro stimulation, gut lavage, bronchioalveolar lavage, nasal lavage, and induced sputum.

The term "fibroproliferative disease" or "fibrotic disease or disorder" refers to conditions involving fibrosis in one or more tissues. As used herein the term "fibrosis" refers to the formation of fibrous tissue as a reparative or reactive process, rather than as a normal constituent of an organ or tissue.

Fibrotic disorders include, but are not limited to, systemic and local scleroderma, keloids and hypertrophic scars, atherosclerosis, restenosis, pulmonary inflammation and fibrosis, interstitial lung disease, idiopathic pulmonary fibrosis, liver cirrhosis, fibrosis as a result of chronic hepatitis B or C infection, radiation-induced fibrosis, fibrosis arising from wound healing, kidney disease, heart disease resulting from scar tissue, and eye diseases such as macular degeneration, and retinal and vitreal retinopathy. Additional fibrotic diseases include fibrosis resulting from chemotherapeutic drugs, radiation-induced fibrosis, and injuries and burns.

The terms "treat", "treating" and "treatment" refer to eliminating, reducing, suppressing or ameliorating, either temporarily or permanently, either partially or completely, a clinical symptom, manifestation or progression of an event, disease or condition associated with an inflammatory disorder described herein. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method for determining the efficacy of treatment comprising administering to a patient therapeutic agent in an amount and for a time sufficient to induce a sustained improvement over baseline of an indicator that reflects the severity of the particular disorder.

The term "therapeutically effective amount" refers to an amount of therapeutic agent that is effective to ameliorate or lessen symptoms or signs of disease associated with a disease or disorder.

Specific Binding Agents

Specific binding agents such as antibodies and antibody fragments that bind to their target antigen, e.g., a surface molecule, a cytokine and the like, are useful in the method of the invention. In one embodiment, the specific binding agent is an antibody. The antibodies may be polyclonal including monospecific polyclonal; monoclonal (MAbs); recombinant; chimeric; humanized, such as complementarity-determining region (CDR)-grafted; human; single chain; and/or bispecific; as well as fragments; variants; or derivatives thereof. Antibody fragments include those portions of the antibody that bind to an epitope on the polypeptide of interest. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Monoclonal antibodies may be modified for use as therapeutics or diagnostics. One embodiment is a "chimeric" antibody in which a portion of the heavy (H) and/or light (L) chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See U.S. Pat. No. 4,816,567; Morrison et al., 1985, Proc. Natl. Acad. Sci. 81:6851-55.

In another embodiment, a monoclonal antibody is a "humanized" antibody. Methods for humanizing non-human antibodies are well known in the art. See U.S. Pat. Nos. 5,585,089 and 5,693,762. Generally, a humanized antibody has one or more amino acid residues introduced into it from a source that is non-human. Humanization can be performed, for example, using methods described in the art (Jones et al., 1986, Nature 321:522-25; Riechmann et al., 1998, Nature 332:323-27; Verhoeyen et al., 1988, Science 239:1534-36), by substituting at least a portion of a rodent complementarity-determining region for the corresponding regions of a human antibody.

Also encompassed by the invention are human antibodies that bind antigens of interest. Using transgenic animals (e.g., mice) that are capable of producing a repertoire of human antibodies in the absence of endogenous immunoglobulin production such antibodies are produced by immunization with a polypeptide antigen (i.e., having at least 6 contiguous amino acids), optionally conjugated to a carrier. See, e.g., Jakobovits et al., 1993, Proc. Natl. Acad. Sci. 90:2551-55; Jakobovits et al., 1993, Nature 362:255-58; Bruggermann et al., 1993, Year in Immuno. 7:33. See also PCT App. Nos. PCT/US96/05928 and PCT/US93/06926. Additional methods are described in U.S. Pat. No. 5,545,807, PCT App. Nos. PCT/US91/245 and PCT/GB89/01207, and in European Patent Nos. 546073B1 and 546073A1. Human antibodies can also be produced by the expression of recombinant DNA in host cells or by expression in hybridoma cells as described herein.

Human antibodies can also be produced from phage-display libraries (Hoogenboom et al., 1991, J. Mol. Biol. 227:381; Marks et al., 1991, J. Mol. Biol. 222:581). These processes mimic immune selection through the display of antibody repertoires on the surface of filamentous bacteriophage, and subsequent selection of phage by their binding to an antigen of choice. One such technique is described in PCT App. No. PCT/US98/17364, which describes the isolation of high affinity and functional agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein. In a preferred embodiment, the antibodies are produced in mammalian host cells, such as CHO cells. Monoclonal (e.g., human) antibodies may be produced by the expression of recombinant DNA in host cells or by expression in hybridoma cells as described herein.

Specific binding agents that bind cytokines useful for detecting T cell populations are contemplated herein, including but not limited to, binding agents specific for IL-4, IL-5, IL-13, IFN-g, TNF-a, IL-2, IL-17A, IL-17F, IL-22, and IL-10.

Specific binding agents that bind to cell surface markers are contemplated for use in identification of T cell subpopulations. Exemplary cell surface markers include, but are not limited to, ST2, CRTH2, and CCR4 for Th2 cells, CXCR3 for Th1 cells, and/or CCR6 for Th17 cells. T cell subpopulations can also be distinguished based on biomarkers indicative of activation state, including PD1, CTLA4, CD40L, ICOS, OX40, 41BB, TIM-3, GITR, HLA-DR and Ki67 of Th1, Th2, and Th17 cells.

Therapeutic Agents

The methods described herein are useful in conjunction with therapeutic agents. Particularly preferred therapeutic agents include antibodies that antagonize cytokines or bind receptors that alter T helper cell or CTL ratios in a patient. Examples include, but are not limited to, antibodies to TSLP, TSLP receptor, IL-25, IL-17A, IL-17-B, IL-17C, IL-17D, IL-17E (aka IL-25), IL-17-F, IL-17RA, IL-17-RB, IL-17RC, IL-17RD, IL-17RE, IL-33, ST2, IL-4, IL-13, IL4/13R, IL-5, IL-5R, TNF, TNF-R, IL-6, IL-6R, IL-10, IL-10R, IL-12p35, IL-12p40, IL-18, IL-18R, IL-22, IL-23/p19, TGF-b, IL-2, IFN-g, IFN-a, IL-1, IL-1R, IL-9, IL-36 and GM-CSF. Also contemplated are chemokines that are chemoattractant for Th cells or CTLs, including but not limited to, CCL17, CCL22, CCL20, IP-10 and others.

Examples of anti-TSLP antibodies that may be used in certain embodiments include, but are not limited to, those described in U.S. Pat. No. 7,982,016, US Publ. Pat. Appl. No. 20090186022, and U.S. Pat. No. 8,232,372. Examples of anti-TSLP receptor antibodies include, but are not limited to, those described in U.S. Pat. No. 8,101,182. In particularly preferred embodiments, the anti-TSLP antibody is the antibody designated as A5 within U.S. Pat. No. 7,982,016.

Examples of anti-IL-17RA antibodies that may be used in certain embodiments include, but are not limited to, those described in U.S. Pat. No. 7,767,206, U.S. Pat. No. 7,786,234, U.S. Pat. No. 7,939,070, U.S. Pat. Nos. 7,833,527, 8,435,518, U.S. Pat. No. 8,545,842, and US Publ. Pat. Appl. No. 20 130022621. Also suitable for use in certain embodiments is the anti-IL-17RA antibody brodalumab as described in *Recommended International Nonproprietary Names: List* 67 (WHO Drug Information, Vol. 26, No. 1, 2012; World Health Organization). Examples of anti-IL-17A antibodies that can be used in certain embodiments include, but are not limited to, perakizumab as described in *Recommended International Nonproprietary Names: List* 69 (WHO Drug Information Vol. 27, No. 1, 2013; World Health Organization), secukinumab as described in *Proposed International Nonproprietary Names: List* 102 (WHO Drug Information, Vol. 23, No. 4, 2009; World Health Organization), ixekizumab as described in *Proposed International*

*Nonproprietary Names: List* 105 (WHO Drug Information, Vol. 25, No. 2, 2011; World Health Organization), and tildakizumab as described in *Recommended International Nonproprietary Names: List* 70 (WHO Drug Information, Vol. 27, No. 3, 2013; World Health Organization).

Examples of anti-ST2 antibodies that may be used in certain embodiments include, but are not limited to, those described in WO2013173761. Particularly preferred are antibodies described as Ab1, Ab2, Ab3, Ab4, Ab5, Ab6, Ab7, Ab8, Ab9, Ab10, Ab11, Ab30, Ab32, and Ab33 therein.

It is contemplated that essentially any antibody may be incorporated into the methods described herein. Exemplary antibodies (and the antigen to which they specifically bind) include, but are not limited to, those described in U.S. Pat. No. 7,947,809 and U.S. Patent Application Publication No. 20090041784 (glucagon receptor), U.S. Pat. No. 7,939,070, U.S. Pat. No. 7,833,527, U.S. Pat. No. 7,767,206, and U.S. Pat. No. 7,786,284 (IL-17 receptor A), U.S. Pat. No. 7,872,106 and U.S. Pat. No. 7,592,429 (Sclerostin), U.S. Pat. No. 7,871,611, U.S. Pat. No. 7,815,907, U.S. Pat. No. 7,037,498, U.S. Pat. No. 7,700,742, and U.S. Patent Application Publication No. 20100255538 (IGF-1 receptor), U.S. Pat. No. 7,868,140 (B7RP1), U.S. Pat. No. 7,807,159 and U.S. Patent Application Publication No. 20110091455 (myostatin), U.S. Pat. No. 7,736,644, U.S. Pat. No. 7,628,986, U.S. Pat. No. 7,524,496, and U.S. Patent Application Publication No. 20100111979 (deletion mutants of epidermal growth factor receptor), U.S. Pat. No. 7,728,110 (SARS coronavirus), U.S. Pat. No. 7,718,776 and U.S. Patent Application Publication No. 20100209435 (OPGL), U.S. Pat. No. 7,658,924 and U.S. Pat. No. 7,521,053 (Angiopoietin-2), U.S. Pat. No. 7,601,818, U.S. Pat. No. 7,795,413, U.S. Patent Application Publication No. 20090155274, U.S. Patent Application Publication No. 20110040076 (NGF), U.S. Pat. No. 7,579,186 (TGF-β type II receptor), U.S. Pat. No. 7,541,438 (connective tissue growth factor), U.S. Pat. No. 7,438,910 (IL1-R1), U.S. Pat. No. 7,423,128 (properdin), U.S. Pat. No. 7,411,057, U.S. Pat. No. 7,824,679, U.S. Pat. No. 7,109,003, U.S. Pat. No. 6,682,736, U.S. Pat. No. 7,132,281, and U.S. Pat. No. 7,807,797 (CTLA-4), U.S. Pat. No. 7,084,257, U.S. Pat. No. 7,790,859, U.S. Pat. No. 7,335,743, U.S. Pat. No. 7,084,257, and U.S. Patent Application Publication No. 20110045537 (interferon-gamma), U.S. Pat. No. 7,932,372 (MAdCAM), U.S. Pat. No. 7,906,625, U.S. Patent Application Publication No. 20080292639, and U.S. Patent Application Publication No. 20110044986 (amyloid), U.S. Pat. No. 7,815,907 and U.S. Pat. No. 7,700,742 (insulin-like growth factor I), U.S. Pat. No. 7,566,772 and U.S. Pat. No. 7,964,193 (interleukin-1β), U.S. Pat. No. 7,563,442, U.S. Pat. No. 7,288,251, U.S. Pat. No. 7,338,660, U.S. Pat. No. 7,626,012, U.S. Pat. No. 7,618,633, and U.S. Patent Application Publication No. 20100098694 (CD40), U.S. Pat. No. 7,498,420 (c-Met), U.S. Pat. No. 7,326,414, U.S. Pat. No. 7,592,430, and U.S. Pat. No. 7,728,113 (M-CSF), U.S. Pat. No. 6,924,360, U.S. Pat. No. 7,067,131, and U.S. Pat. No. 7,090,844 (MUC18), U.S. Pat. No. 6,235,883, U.S. Pat. No. 7,807,798, and U.S. Patent Application Publication No. 20100305307 (epidermal growth factor receptor), U.S. Pat. No. 6,716,587, U.S. Pat. No. 7,872,113, U.S. Pat. No. 7,465,450, U.S. Pat. No. 7,186,809, U.S. Pat. No. 7,317,090, and U.S. Pat. No. 7,638,606 (interleukin-4 receptor), U.S. Patent Application Publication No. 20110135657 (BETAKLOTHO), U.S. Pat. No. 7,887,799 and U.S. Pat. No. 7,879,323 (fibroblast growth factor-like polypeptides), U.S. Pat. No. 7,867,494 (IgE), U.S. Patent Application Publication No. 20100254975 (ALPHA-4 BETA-7), U.S. Patent Application Publication No. 20100197005 and U.S. Pat. No. 7,537,762 (ACTIVIN RECEPTOR-LIKE KINASE-1), U.S. Pat. No. 7,585,500 and U.S. Patent Application Publication No. 20100047253 (IL-13), U.S. Patent Application Publication No. 20090263383 and U.S. Pat. No. 7,449,555 (CD148), U.S. Patent Application Publication No. 20090234106 (ACTIVIN A), U.S. Patent Application Publication No. 20090226447 (angiopoietin-1 and angiopoietin-2), U.S. Patent Application Publication No. 20090191212 (Angiopoietin-2), U.S. Patent Application Publication No. 20090155164 (C-FMS), U.S. Pat. No. 7,537,762 (activin receptor-like kinase-1), U.S. Pat. No. 7,371,381 (galanin), U.S. Patent Application Publication No. 20070196376 (INSULIN-LIKE GROWTH FACTORS), U.S. Pat. No. 7,267,960 and U.S. Pat. No. 7,741,115 (LDCAM), US7265212 (CD45RB), U.S. Pat. No. 7,709,611, U.S. Patent Application Publication No. 20060127393 and U.S. Patent Application Publication No. 20100040619 (DKK1), U.S. Pat. No. 7,807,795, U.S. Patent Application Publication No. 20030103978 and U.S. Pat. No. 7,923,008 (osteoprotegerin), U.S. Patent Application Publication No. 20090208489 (OV064), U.S. Patent Application Publication No. 20080286284 (PSMA), U.S. Pat. No. 7,888,482, U.S. Patent Application Publication No. 20110165171, and U.S. Patent Application Publication No. 20110059063 (PAR2), U.S. Patent Application Publication No. 20110150888 (HEPCIDIN), U.S. Pat. No. 7,939,640 (B7L-1), U.S. Pat. No. 7,915,391 (c-Kit), U.S. Pat. No. 7,807,796, U.S. Pat. No. 7,193,058, and U.S. Pat. No. 7,427,669 (ULBP), U.S. Pat. No. 7,786,271, U.S. Pat. No. 7,304,144, and U.S. Patent Application Publication No. 20090238823 (TSLP), U.S. Pat. No. 7,767,793 (SIGIRR), U.S. Pat. No. 7,705,130 (HER-3), U.S. Pat. No. 7,704,501 (ataxin-1-like polypeptide), U.S. Pat. No. 7,695,948 and U.S. Pat. No. 7,199,224 (TNF-α converting enzyme), U.S. Patent Application Publication No. 20090234106 (ACTIVIN A), U.S. Patent Application Publication No. 20090214559 and U.S. Pat. No. 7,438,910 (IL1-R1), U.S. Pat. No. 7,579,186 (TGF-β type II receptor), U.S. Pat. No. 7,569,387 (TNF receptor-like molecules), U.S. Pat. No. 7,541,438, (connective tissue growth factor), U.S. Pat. No. 7,521,048 (TRAIL receptor-2), U.S. Pat. No. 6,319,499, U.S. Pat. No. 7,081,523, and U.S. Patent Application Publication No. 20080182976 (erythropoietin receptor), U.S. Patent Application Publication No. 20080166352 and U.S. Pat. No. 7,435,796 (B7RP1), U.S. Pat. No. 7,423,128 (properdin), U.S. Pat. No. 7,422,742 and U.S. Pat. No. 7,141,653 (interleukin-5), U.S. Pat. No. 6,740,522 and U.S. Pat. No. 7,411,050 (RANKL), U.S. Pat. No. 7,378,091 (carbonic anhydrase IX (CA IX) tumor antigen), U.S. Pat. No. 7,318,925 and U.S. Pat. No. 7,288,253 (parathyroid hormone), U.S. Pat. No. 7,285,269 (TNF), U.S. Pat. No. 6,692,740 and U.S. Pat. No. 7,270,817 (ACPL), U.S. Pat. No. 7,202,343 (monocyte chemo-attractant protein-1), U.S. Pat. No. 7,144,731 (SCF), U.S. Pat. No. 6,355,779 and U.S. Pat. No. 7,138,500 (4-1BB), U.S. Pat. No. 7,135,174 (PDGFD), U.S. Pat. No. 6,630,143 and U.S. Pat. No. 7,045,128 (Flt-3 ligand), U.S. Pat. No. 6,849,450 (metalloproteinase inhibitor), U.S. Pat. No. 6,596,852 (LERK-5), U.S. Pat. No. 6,232,447 (LERK-6), U.S. Pat. No. 6,500,429 (brain-derived neurotrophic factor), U.S. Pat. No. 6,184,359 (epithelium-derived T-cell factor), U.S. Pat. No. 6,143,874 (neurotrophic factor NNT-1), U.S. Patent Application Publication No. 20110027287 (PROPROTEIN CONVERTASE SUBTILISIN KEXIN TYPE 9 (PCSK9)), U.S. Patent Application Publication No. 20110014201 (IL-18 RECEPTOR), and U.S. Patent Application Publication No. 20090155164 (C-FMS). The above patents and published patent applications are incorporated herein by reference in their entirety for purposes of their disclosure of antibody polypeptides, antibody encoding nucleic acids, host cells, vectors, methods of making antibodies, pharmaceutical compositions, and methods of treating diseases associated with the respective target of the antibody.

Therapeutic Indications

The method of the invention is useful to detect T cell subsets, such as Th1, Th2 and Th17 cells, in subjects having a broad range of disease or disorders that have an immune component, i.e., involvement of immune cells in development or progression of the disease or disorder.

Asthma:

Asthma is a chronic inflammatory disorder of the airways. Each year, asthma accounts for an estimated 1.1 million outpatient visits, 1.6 million emergency room visits, 444,000 hospitalizations (Defrances et al, 2008) Available at: http://www.cdc.gov/nchs/data/nhsr/nhsr005.pdf, and 3,500 deaths in the U.S. In susceptible individuals, asthmatic inflammation causes recurrent episodes of wheezing, breathlessness, chest tightness, and cough. The etiology of asthma is thought to be multi-factorial, influenced by both genetic environmental mechanisms,[1,2] with environmental allergens an important cause.[2,3] The majority of cases arise when a person becomes hypersensitive to allergens (atopy). Atopy is characterized by an increase in Th2 cells and Thh2 cytokine expression and IgE production. Approximately 10 million patients in the United States are thought to have allergy-induced asthma. Despite the available therapeutic options, asthma continues to be a major health problem. Worldwide, asthma currently affects approximately 300 million people; by 2020, asthma is expected to affect 400 million people (Partridge, Eur Resp Rev. 16:67-72, 2007).

Allergen inhalation by atopic asthmatics induces some of the manifestations of asthma, including reversible airflow obstruction, airway hyperresponsiveness, and eosinophilic and basophilic airway inflammation. Allergen inhalation challenge has become the predominant model of asthma in many species (Bates et al., Am J Physiol Lung Cell Mol Physiol. 297(3):L401-10, 2009; Diamant et al., J Allergy Clin Immunol. 132(5):1045-1055, 2013.)

Different asthma subtypes that are refractive to steroid treatment have been identified. Eosinophils are important inflammatory cells in allergic asthma that is characteristically mediated by Th2-type CD4+ T cells. Neutrophilic airway inflammation is associated with corticosteroid treatment in severe asthma and can be mediated by Th1- or Th17-type T cells (Mishra et al. Dis. Model. Mech. 6:877-888, 2013).

Thymic stromal lymphopoietin (TSLP) is an epithelial cell-derived cytokine that is produced in response to pro-inflammatory stimuli and drives allergic inflammatory responses primarily through its activity on dendritic cells (Gilliet, J Exp Med. 197:1059-1067, 2003; Soumelis, Nat Immunol. 3:673-680, 2002; Reche, J Immunol. 167:336-3432001), mast cells (Allakhverdi, J Exp Med. 204:253-258, 2007) and CD34+ progenitor cells.[9] TSLP signals through a heterodimeric receptor consisting of the interleukin (IL)-7 receptor alpha (IL-7Rα) chain and a common γ chain-like receptor (TSLPR) (Pandey, Nat Immunol. 1:59-64, 2000; Park, J Exp Med. 192:659-669, 2000).

Human TSLP mRNA[10,11] and protein levels[11] are increased in the airways of asthmatic individuals compared to controls, and the magnitude of this expression correlates with disease severity.[10] Recent studies have demonstrated association of a single nucleotide polymorphism in the human TSLP locus with protection from asthma, atopic asthma and airway hyperresponsiveness, suggesting that differential regulation of TSLP gene expression might influence disease susceptibility.[1,12,13] These data suggest that targeting TSLP may inhibit multiple biological pathways involved in asthma.

Fibrotic Disorders:

Fibrosis is characterized by fibroblast accumulation and collagen deposition in excess of normal deposition in any particular tissue. Fibroblasts are connective tissue cells, which are dispersed in connective tissue throughout the body. Fibroblasts secrete a nonrigid extracellular matrix containing type I and/or type III collagen. In response to an injury to a tissue, nearby fibroblasts migrate into the wound, proliferate, and produce large amounts of collagenous extracellular matrix. Collagen is a fibrous protein rich in glycine and proline that is a major component of the extracellular matrix and connective tissue, cartilage, and bone. Collagen molecules are triple-stranded helical structures called .alpha.-chains, which are wound around each other in a ropelike helix. Collagen exists in several forms or types; of these, type I, the most common, is found in skin, tendon, and bone; and type III is found in skin, blood vessels, and internal organs.

Fibrotic disorders include, but are not limited to, systemic and local scleroderma, keloids and hypertrophic scars, atherosclerosis, restenosis, pulmonary inflammation and fibrosis, interstitial lung disease, idiopathic pulmonary fibrosis, liver cirrhosis, fibrosis as a result of chronic hepatitis B or C infection, radiation-induced fibrosis, fibrosis arising from wound healing, kidney disease, heart disease resulting from scar tissue, and eye diseases such as macular degeneration, and retinal and vitreal retinopathy. Additional fibrotic diseases include fibrosis resulting from chemotherapeutic drugs, radiation-induced fibrosis, and injuries and burns.

Scleroderma:

Scleroderma is a fibrotic disorder characterized by a thickening and induration of the skin caused by the overproduction of new collagen by fibroblasts in skin and other organs. Scleroderma may occur as a local or systemic disease. Systemic scleroderma may affect a number of organs. Systemic sclerosis is characterized by formation of hyalinized and thickened collagenous fibrous tissue, with thickening of the skin and adhesion to underlying tissues, especially of the hands and face. The disease may also be characterized by dysphagia due to loss of peristalsis and submucosal fibrosis of the esophagus, dyspnea due to pulmonary fibrosis, myocardial fibrosis, and renal vascular changes. (Stedman's Medical Dictionary, 26.sup.th Edition, Williams & Wilkins, 1995)). Pulmonary fibrosis affects 30 to 70% of scleroderma patients, often resulting in restrictive lung disease (Atamas et al. Cytokine and Growth Factor Rev 14: 537-550 (2003)). Idiopathic pulmonary fibrosis is a chronic, progressive and usually lethal lung disorder, thought to be a consequence of a chronic inflammatory process (Kelly et al., Curr Pharma Design 9: 39-49 (2003)).

Lupus:

Systemic Lupus Erythematosus (SLE) is an autoimmune disease caused by recurrent injuries to blood vessels in multiple organs, including the kidney, skin, and joints. SLE is estimated to affect over 500,000 people in the United States. In patients with SLE, a faulty interaction between T cells and B cells results in the production of autoantibodies that attack the cell nucleus. These include anti-double stranded DNA and anti-Sm antibodies. Autoantibodies that bind phospholipids are also found in about half of SLE patients, and are responsible for blood vessel damage and low blood counts. Immune complexes accumulate the kidneys, blood vessels, and joints of SLE patients, where they cause inflammation and tissue damage. It has been hypothesized that Th2 cells in contribute to overproduction of autoantibodies.

Lupus also includes subacute cutaneous lupus (SCLE). Other disorders in which autoantibodies play a role include, Sjogren's syndrome and Immune thrombocytopenic purpura (ITP).

Cancer:

Recent research has shown that many cancers have an immune component that contributes to both progression of disease as well as killing of tumor cells. Certain cancers have been associated with skewing toward a Th1 or Th2 phenotype. Th1-like cells are typically involved in promoting cell-mediated immunity, initiating a cytotoxic response and generally are considered one of the host's important anti-cancer mechanism. It has been shown that the Th1 cytokine IFN-g can promote anti-tumor activity in vivo (Ikeda et al., Cytokine Growth Factor Rev. 13:95-109, 2002). Ito et al. (Anticancer Research 25:2027-2031, 2005) describe that in non-small cell lung carcinoma patients, subjects with a low Th1/Th2 ratio in peripheral blood had a significantly better prognosis than those with a high Th1/Th2 ratio in Stage II or III cancer. Dai et al. (J Immunother. 36(4):248-57, 2013) demonstrated that clearance of ovarian tumors and melanoma tumors in a mouse model was associated with a shift from a Th2 environment to a cytotoxic Th1 environment. Additionally, Th17 cells have been shown to be cytotoxic for tumor cells in certain studies, but also can be indicators of unfavorable outcomes in other studies (Muranski et al., Blood 121:2402-2414, 2013). The methods herein are useful to identify the Th population skewing in cancer before and after treatment and to alter administration of cancer therapeutics in order to skew the Th1 population to one which will promote regression of tumors in a subject.

Exemplary cancers contemplated herein include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, urinary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and Wilm's Tumor. In some embodiments, the tumor is associated with a cancer selected from the group consisting of breast cancer, melanoma, prostate cancer, pancreatic cancer, head and neck cancer, lung cancer, non small-cell lung carcinoma, renal cancer, colorectal cancer, colon cancer, ovarian cancer, liver cancer and gastric cancer. In some embodiments, the cancer is pancreatic cancer.

Additional diseases, disorders, or conditions contemplated by the method herein include, but are not limited to, inflammation, autoimmune disease, cartilage inflammation, fibrotic disease and/or bone degradation, arthritis, rheumatoid arthritis, juvenile arthritis, juvenile rheumatoid arthritis, pauciarticular juvenile rheumatoid arthritis, polyarticular juvenile rheumatoid arthritis, systemic onset juvenile rheumatoid arthritis, juvenile ankylosing spondylitis, juvenile enteropathic arthritis, juvenile reactive arthritis, juvenile Reiter's Syndrome, SEA Syndrome (Seronegativity, Enthesopathy, Arthropathy Syndrome), juvenile dermatomyositis, juvenile psoriatic arthritis, juvenile scleroderma, juvenile systemic lupus erythematosus, juvenile vasculitis, pauciarticular rheumatoid arthritis, polyarticular rheumatoid arthritis, systemic onset rheumatoid arthritis, ankylosing spondylitis, enteropathic arthritis, reactive arthritis, Reiter's Syndrome, SEA Syndrome (Seronegativity, Enthesopathy, Arthropathy Syndrome), dermatomyositis, psoriatic arthritis, scleroderma, systemic lupus erythematosus, vasculitis, myolitis, polymyolitis, dermatomyolitis, osteoarthritis, polyarteritis nodossa, Wegener's granulomatosis, arteritis, ploymyalgia rheumatica, sarcoidosis, scleroderma, sclerosis, primary biliary sclerosis, sclerosing cholangitis, Sjogren's syndrome, psoriasis, plaque psoriasis, guttate psoriasis, inverse psoriasis, pustular psoriasis, erythrodermic psoriasis, dermatitis, atopic dermatitis, atherosclerosis, Still's disease, Systemic Lupus Erythematosus (SLE), multiple sclerosis, myasthenia gravis, inflammatory bowel disease (IBD), Crohn's disease, ulcerative colitis, celiac disease, multiple schlerosis (MS), asthma, COPD, Guillain-Barre disease, Type I diabetes mellitus, Graves' disease, Addison's disease, Raynaud's phenomenon, autoimmune hepatitis, GVHD, and the like.

Labels

In some embodiments, the antibody substance is labeled to facilitate its detection. A "label", "detectable label" or a "detectable moiety" is a composition detectable by spectroscopic, photochemical, biochemical, immunochemical, chemical, or other physical means. For example, labels suitable for use in the present disclosure include, radioactive labels (e.g., 32P), fluorophores (e.g., fluorescein), electron dense reagents, enzymes (e.g., as commonly used in an ELISA), biotin, digoxigenin, or haptens as well as proteins which can be made detectable, e.g., by incorporating a radiolabel into the hapten or peptide, or used to detect antibodies specifically reactive with the hapten or peptide.

Examples of labels include, but are not limited to, fluorescent dyes described herein, radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold, colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugation of an active agent according to the disclosure. In one aspect of the present disclosure, the bifunctional isocyanate reagents of the disclosure can be used to conjugate a label to a biopolymer to form a label biopolymer conjugate without an active agent attached thereto. The label biopolymer conjugate may be used as an intermediate for the synthesis of a labeled conjugate according to the disclosure or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound.

The compounds of the present disclosure can also be conjugated directly to signal-generating compounds, e.g., by conjugation with an enzyme or fluorophore. Enzymes suitable for use as labels include, but are not limited to, hydrolases, particularly phosphatases, esterases and glycosidases, or oxidatases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present disclosure, see U.S. Pat. No. 4,391,904.

Methods

The present disclosure provides a whole blood stimulation method that allows measurement of cell-signaling changes in T cell populations, such as Th1/Th2/Th17/Th22 cell and/or CTL subsets, in the context of therapy with a therapeutic agent. For example, the disclosure demonstrates skewing away from a Th2 profile in asthmatics treated with anti-TSLP neutralizing antibody. Further, determining the cytokine expression profile at baseline is useful to characterize a sub-population of patients receiving treatment and adjust levels of therapeutic administration for patients. This assay is useful to evaluate T cell subsets in clinical trials in multiple inflammatory diseases. This specific application has not previously been demonstrated in human clinical trials.

The methods herein provide for detecting a ratio of Th2 and Th1 cells in a sample from a patient comprising measuring levels of Th2-specific and Th1-specific cytokines, the method comprising a) contacting the sample with i) two or more specific binding agents that bind two or more Th2 cytokines, wherein the two or more specific binding agents for the Th2-specific cytokines are labeled with a first fluorophore; and ii) at least one specific binding agent that binds a Th1 cytokine, wherein the specific binding agent for the Th1 cytokine is labeled with a second fluorophore that is different from the first fluorophore; b) measuring levels of the first and second fluorophores in the sample and designating the cell as a Th1 or Th2 cell based on the level of Th1-specific and Th2-specific fluorophore detected; and c) determining the ratio of Th2 to Th1 cells in a sample. The method is optionally carried out to determine the ratio of Th17 cells, wherein the Th17 cytokines are labeled with a third fluorophore as described herein.

The method is also adapted to determine the ratio of Th1/Th17 cells and Th2/Th17 cells. It is also contemplated that the converse ratio, i.e., reverse of the numerator and denominator for a stated ratio herein, is calculated using the method above.

In various embodiments, the Th2 cytokines are selected from the group consisting of IL-4, IL-5 and IL-13. In some embodiments, the Th1 cytokines are selected from the group consisting of interferon gamma (IFN-g), tumor necrosis factor alpha (TNF-a) and IL-2. In various embodiments, the Th17 cytokines are selected from the group consisting of IL-17A, IL-17F, IFN-g and IL-22. In various embodiments, the specific binding agent is an antibody specific for a Th1-specific, Th2-specific or Th17-specific cytokine.

Also contemplated are methods of detecting CD8+ CTLs. The present disclosure provides a method for detecting a subset of CTL, such as polyfunctional CTLs, the method comprising a) contacting the sample with one or more specific binding agents that bind one or more polyfunctional CTL cytokines, wherein the one or more specific binding agents for the polyfunctional CTL cytokines are labeled with a first fluorophore and/or second fluorophore and/or third fluorophore; b) measuring levels of the first and second and/or third fluorophores in the sample and designating the cell as a polyfunctional CTL cell based on the level of specific fluorophore detected; and c) determining the ratio of polyfunctional CTL to other T cells, e.g., Th, Treg, NKT or gdT, in a sample.

In various embodiments, polyfunctional CTL cytokines are selected from the group consisting of IFN-g, IL-17, TNF-a and IL-2.

In one embodiment the cytokines are contacted intracellularly. Contacting intracellulary is carried out following protocols as described in the art for intracellular staining for flow cytometry (See e.g., Warrington et al., Arthritis Res Ther. 8(4):R136, 2006; Ito et al., Anticancer Research 25:2027-2031, 2005). Briefly, cells are obtained from a sample and fixed and permeabilized, e.g., using a fixation permeabilization buffer. The cells are then contacting the cells with a specific binding agent that binds a target antigen such as a cytokine. The cells are optionally stimulated in vitro using PMA/ionomycin or another stimulant prior to fixation as described in the Examples.

In some embodiments, the cytokines are contacted extracellularly. In certain embodiments, the cytokines are secreted from the cells in vitro or in are detectable in fluid samples. The sample fluid can then be contacted with specific binding agents that bind a cytokine of interest and the level of cytokine determined, wherein the level of cytokine is predictive of the skewing to the particular Th1, Th2 or Th17 phenotype or CTL population in the subject sample. If cells are stimulated in vitro, cytokines excreted into the fluid could be measured.

It is contemplated that the sample is obtained at various times before and after administration of a therapeutic agent. Obtaining a sample concurrent with administration of a therapeutic agent does not require that the agent be administered at the same time as obtaining the sample, as long as there is an overlap in the time period during which the agents are exerting their therapeutic effect. Simultaneous or sequential timing is contemplated.

In certain embodiments, the relative number (percentage) of Th1, Th2, T17 cells or CTLs is compared at various times before and after administration of a therapeutic agent. In certain embodiments, administration of the therapeutic agent causes a decrease in the relative number of Th2 cells present in samples collected from a subject.

It is contemplated that the agent is administered concurrently with obtaining a sample for analysis, with concurrently referring to agents given within 30 minutes before or after obtaining the sample.

In another aspect, the therapeutic agent is administered prior to obtaining the sample. Prior administration refers to administration of the agent within the range of one week prior to obtaining the sample, up to 30 minutes before obtaining the sample. It is further contemplated that the agent is administered subsequent to obtaining the sample. Subsequent administration is meant to describe administration from 30 minutes after treatment up to one week after therapeutic administration.

In certain embodiments, the therapeutic agent is administered for one week, two weeks, three weeks, four weeks, six weeks, two months, three months or more prior to obtaining the sample.

In various embodiments, the asthma patient has atopic asthma or mild asthma. In certain embodiments, the Th2/Th1 ratio is skewed toward the Th2 phenotype and this skewing could identify the patient as a candidate for treatment with a therapeutic agent that targets the Th2 pathway. In various embodiments, the patient may be a candidate for Th2 targeted therapy if the ratio of Th2/Th1 cells is approximately 0.2 or higher.

In certain embodiments, the patient is identified as responsive to treatment of asthma if the ratio of Th2/Th1 cells decreases by 20%, 30%, 40%, 50%, 60% or more. In various embodiments, the ratio of Th2/Th1 cells decreases by 20%, 25%, 30%, 35%, 40%, 45%, 50%, 55%, 60%, 65%, 70%, 75%, 80%, 85% or 90%, or within the range of 20-40%, 40-60%, 60-80% or 50-90%. In one embodiment, a Th2/Th1 ratio at which the patient is identified as responsive to treatment is approximately 0.1 or below.

In various embodiments, the disclosure provides a method of altering the dose regimen of an anti-TSLP agent in treating an immune disorder comprising determining the ratio of Th2/Th1 and/or Th17 cells in a sample and altering the dose of anti-TSLP antibody if the ratio of Th2/Th1 and/or Th17 cells changes during treatment, wherein the dose of therapeutic is increased if the ratio of Th2/Th1 cells is stable or increases indicating skewing towards Th2 profile (i.e., increasing the proportion of Th2 cells and/or decreasing the proportion of Th1 cells); and wherein the dose of therapeutic is decreased if the ratio of Th2/Th1 cells decreases indicating reduction in Th2 profile (i.e., decreasing the proportion of Th2 cells and/or increasing the proportion of Th1 cells). In certain embodiments, the dose regimen is not altered. Rather, the dose regimen is continued as a result of the present assay.

In one embodiment, the present method provides a validation protocol for a 7-color intracellular cytokine assay for Th1, Th2 and Th17 cells by flow cytometry and a six color immunophenotyping panel for Th17 cell surface markers and memory T cell subsets in whole blood. In certain embodiments, the percentage of Th2 cytokine producing cells ranges from 1 to 5%. While unstimulated samples showed a background level of 0.16% it was found that pre-incubation with unlabeled detector antibodies to block staining suggested a lower limit of 0.5%. Longitudinal sampling as well as spike-recovery experiments using isolated CRTH2+ cells suggests the assay is sensitive enough to detect changes in Th2 cells over time.

In one embodiment, the assay is a whole blood flow cytometry method to measure cytokine production (specifically, IL-2, IL-4-5-13, 1L-17A, IL-22, IFN-y, TNF-a) from specific cell populations in human peripheral blood samples. This method was used to demonstrate reduction of Th2-specific intracellular cytokine production and change in the Th2/Th1 ratio by a TSLP-specific antibody in an inhaled allergen challenge study in asthmatic subjects. The described assay has utility in demonstrating pharmacodynamic activity, dose selection, and patient stratification for anti-inflammatory therapies, such as anti-TSLP antibodies, and for immune related disorders broadly.

The method is also useful to determine if skewing away from or toward Th2-specific cytokine plays a role in the efficacy of treatment, e.g., using an anti-TSLP antibody. The method can determine if levels of IL-4, IL-5 or 11-13 are changed in the treated patient and how therapeutic administration can be changed to maximize therapeutic benefit.

Administration and Dosing

In one aspect, methods of the present disclosure include a step of administering a therapeutic agent, optionally in a pharmaceutically acceptable carrier or excipient. In certain embodiments, the pharmaceutical composition is a sterile composition.

Administration is performed using any medically-accepted means for introducing a therapeutic directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, and intracisternal injections, as well as catheter or infusion techniques. Administration by, intradermal, intramammary, intraperitoneal, intrathecal, retrobulbar, intrapulmonary injection and or surgical implantation at a particular site is contemplated as well.

In one embodiment, administration is performed systemically or at the site of a cancer, fibrosis or affected tissue needing treatment by direct injection into the site or via a sustained delivery or sustained release mechanism, which can deliver the formulation internally. For example, biodegradable microspheres or capsules or other biodegradable polymer configurations capable of sustained delivery of a composition (e.g., a soluble polypeptide, antibody, or small molecule) can be included in the formulations of the disclosure implanted near or at site of cancer, fibrosis or affected tissue or organ.

Therapeutic compositions may also be delivered to the patient at multiple sites. The multiple administrations may be rendered simultaneously or may be administered over a period of time. In certain cases it is beneficial to provide a continuous flow of the therapeutic composition. Additional therapy may be administered on a period basis, for example, hourly, daily, weekly, every 2 weeks, every 3 weeks, monthly, or at a longer interval.

Also contemplated in the present disclosure is the administration of multiple agents, such as an antibody composition in conjunction with a second agent as described herein, including but not limited to a an anti-inflammatory agent, a chemotherapeutic agent or an agent useful to treat fibrosis.

The amounts of therapeutic agent, such as an antibody, in a given dosage may vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day. These concentrations may be administered as a single dosage form or as multiple doses. Standard dose-response studies, first in animal models and then in clinical testing, reveal optimal dosages for particular disease states and patient populations.

It will also be apparent that dosing may be modified if traditional therapeutics are administered in combination with therapeutics of the disclosure.

Kits

As an additional aspect, the disclosure includes kits which comprise one or more compounds or compositions packaged in a manner which facilitates their use to practice methods of the disclosure. In one embodiment, such a kit includes a compound or composition described herein (e.g., a composition comprising a specific binding agent alone or affixed to a label or fluorophore), packaged in a container such as a sealed bottle or vessel, with a label affixed to the container or included in the package that describes use of the compound or composition in practicing the method. Preferably, the compound or composition is packaged in a unit dosage form.

Additional aspects and details of the disclosure will be apparent from the following examples, which are intended to be illustrative rather than limiting.

EXAMPLES

Example 1

Materials and Methods
Study Participants
Eligible participants were nonsmoking men and women aged 18 to 60 years with mild stable atopic asthma confirmed by positive skin-prick test, forced expiratory volume (FEV) in 1 second ($FEV_1$)≥70% of predicted, and airway hyperresponsiveness. Participants were tested out of season for pollens affecting their asthma and had no other lung disease. No asthma controller treatments were allowed; inhaled short-acting $\beta_2$ agonists as rescue treatments used less than twice weekly were permitted. All other asthma medications were discontinued at least 4 weeks before enrollment. Participants were excluded for worsening of asthma, respiratory-related visits to the emergency department within 6 weeks, prior use of AMG 157, or known sensitivity to any AMG 157 excipients.

Study Design and Oversight

This proof-of-concept, randomized, double-blind, placebo-controlled study was conducted in 5 centers in Canada. Participants were randomly assigned by interactive voice response system 1:1 to receive 700 mg AMG 157 or placebo by 1-hour intravenous infusion on study days 1, 29, and 57. Allergen and methacholine inhalation challenges were performed at days −15, −14 and −13, days 41, 42 43, 83, 84 and 85. Fractional exhaled nitric oxide (FENO) levels were measured on days −15, −13, 1, 41, 43, 83 and 85, induced sputum was measured on days −15, −14, −13, 1, 41, 42, 43, 83, 84 and 85, and blood samples were measured on days −15, 1, 29, 43, 57, 85, 113 and 169. The primary endpoint was the late asthmatic response (LAR) measured between 3 and 7 hours after the allergen challenge expressed as maximum percent fall in $FEV_1$ and area under the curve (AUC) of the time-adjusted percent fall in $FEV_1$ (% FEV1-time AUC). The secondary endpoints were the LAR measured by minimum $FEV_1$ and AUC of the time-adjusted minimum $FEV_1$ (FEV1-time AUC), early asthmatic response (EAR) measured between 0 and 2 hours after the allergen challenge, and the safety, side-effect profile and immunogenicity of AMG 157. Exploratory endpoints included sputum and blood eosinophils, FENO, Th2 cytokines, Th2/Th1 cell ratio and total IgE in blood, and methacholine $PC_{20}$. Safety evaluations included incidence and severity of adverse events, changes in electrocardiogram, laboratory profiles, vital signs and the presence of anti-AMG 157 antibodies.

The study protocol was approved by the institutional research ethics committees at each participating center, and all participants provided written informed consent.

Laboratory Procedures

The allergen for inhalation was selected using results from skin-prick testing. The allergen inhalation challenge was performed as described.[14] During a screening challenge on day −14, doubling concentrations of allergen were inhaled over 2 minutes by tidal breathing from a Wright nebulizer (Roxon, Quebec) filled with 2-3 mL solution, until a ≥20% fall in $FEV_1$ at 10 minutes post-allergen was reached. The $FEV_1$ was then measured at regular intervals for 7 hours. The EAR (0-2 hours) and LAR (3-7 hours) endpoints were calculated. Selection of allergen dose and methacholine challenges were performed as described.[15] Venous blood was sampled for leukocytes, total IgE and cytokines, and airway eosinophils were sampled from induced sputum using a standard method.[16] FENO measurements followed American Thoracic Society guidelines.[17]

Statistical Analysis

A sample size of 30 (15 per treatment arm) participants was selected based upon empirical evidence from previous studies[18-20] suggesting that 15 participants per treatment group would provide adequate power to differentiate the LAR-attenuating effect of AMG 157 placebo. The analysis population for each endpoint included all available data from all randomized participants who received at least 1 dose of AMG 157 or placebo, with data analyzed in accordance with the initial treatment received. The EAR and LAR were analyzed using a repeated measures analysis of covariance (ANCOVA) including treatment and visit as independent variables, treatment by visit interaction term, and corresponding pre-dose measure as a model covariate. The mean treatment difference, the corresponding 95% confidence interval (CI), and two-sided P value were estimated and reported at each visit. The exploratory endpoints were analyzed using repeated measures ANCOVA (Supplemental Appendix). The summary data are reported as mean±SEM, log normally distributed endpoints are presented as geometric means (95% CI) while categorical data are presented as number (%).

Results

Study Population

A total of 31 participants were randomized, with 16 assigned to AMG 157 and 15 to placebo. All participants received at least one dose of study drug in accordance with the randomization schedule. The study was carried out for approximately 18 months. Twenty-eight participants (90%) completed the full intervention period, and 27 (87%) completed the study. Three of the 4 participants who did not complete the study were lost to follow-up (2 placebo, 1 AMG 157) and 1 participant withdrew at day 34 due to worsening of asthma (AMG 157). One participant from each group did not complete the day 84 allergen challenge, and one participant aborted the day 84 allergen challenge before LAR measurement (AMG 157). Demographics and inhaled allergens were similar in the two groups, and there were no significant differences in any of the baseline variables measured between the two groups.

Endpoints

AMG 157 treatment partially attenuated both the LAR and EAR relative to placebo at days 42 and 84 in each of the 4 allergen challenge endpoints (FIG. 1, FIG. 2). A statistically significant AMG 157-associated attenuation was achieved on the LAR minimum $FEV_1$ and $FEV_1$-time adjusted $AUC_{3-7\ h}$ on day 42, and on the LAR maximum percent fall in $FEV_1$ and minimum $FEV_1$ on day 84, with no additional benefit of the last injection. The maximum percentage decrease in the FEV1 during the late response was 34.0% smaller in the AMG-157 group than in the placebo group on day 42 (P=0.09) and 45.9% smaller (a decrease of 11.7% vs. 21.6%) on day 84 (P=0.02). Patients in the AMG-157 group, as compared with those in the placebo group, had a significant increase in the minimum FEV1 (P=0.01) and in the AUC of the time-adjusted minimum $FEV_1$ (P=0.02) during the late response on day 42 and in the minimum $FEV_1$ (P=0.01) on day 84. In addition, during the early response, the AUC of the time-adjusted percent decrease in the $FEV_1$ was significantly smaller and the AUC of the time-adjusted minimum $FEV_1$ significantly greater in the AMG-157 group than in the placebo group (P=0.03 for both comparisons) on day 42, and the AUC of the time-adjusted percent decrease in the $FEV_1$ was significantly smaller on day 84 (P=0.030) (FIGS. 1 and 2).

Figure 3:
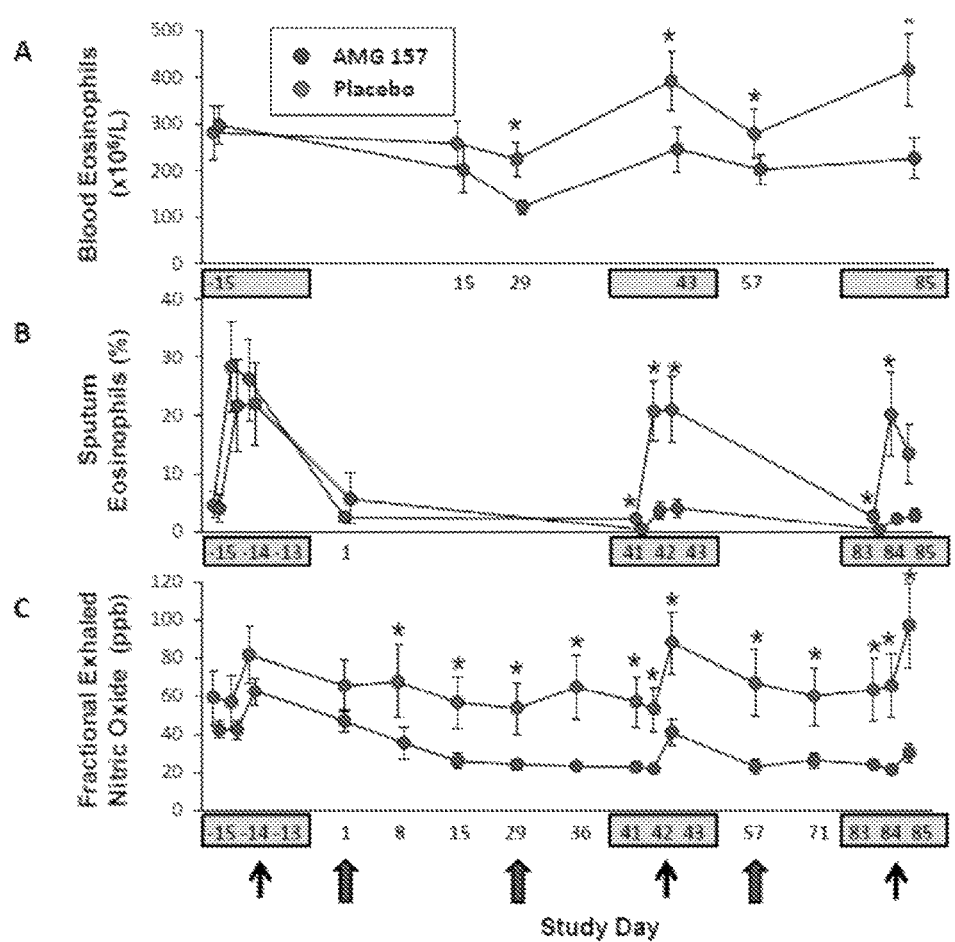
FIGS. 3A to 3C show changes in peripheral blood and sputum eosinophils and the fraction of exhaled nitric oxide. Peripheral blood eosinophils (FIG. 3A), sputum eosinophils (FIG. 3B) and fractional exhaled nitric oxide (FIG. 3C) were measured from pre-dosing baseline on day −15 until day 85. Data are shown as mean±SEM. FEeNO denotes fractional exhaled nitric oxide, red arrows denote dosing, black arrows denote allergen inhalation challenge, * denotes p<0.05 AMG 157 compared to placebo.

The mean baseline blood eosinophil counts decreased from 296.5±40.2×10⁶/L at day −15 to 121.9±14.7×10⁶/L at day 29 with AMG 157, and from 281.1±57.3×10⁶/L at day −15 to 224.1±36.5×10⁶/L at day 29 with placebo. (FIG. 3A). Blood eosinophil counts increased post-allergen on days 43 and 85, however the levels were significantly lower with AMG 157 treatment relative to placebo (overall treatment effect P=0.004).

AMG 157 treatment decreased sputum eosinophils before and after allergen challenge. Mean pre-allergen sputum eosinophil levels were reduced from 4.1±2.3% on day −15, to 0.4±0.1% on day 41 and 0.4±0.1% on day 83. Compared to placebo, AMG 157 significantly reduced pre-allergen sputum eosinophil levels over the course of the study (overall treatment effect P=0.015) (FIG. 3B), and significantly attenuated allergen-induced changes 24 hours post-challenge (overall treatment effect P=0.004).

F$_E$NO was elevated in both treatment groups under baseline conditions. Compared to placebo, AMG 157 treatment significantly decreased F$_E$NO throughout the study (overall treatment effect P=0.002) and significantly attenuated allergen-induced changes 24 hours post challenge (overall treatment effect P=0.02) (FIG. 3C).

Treatment with AMG 157 did not significantly change the pre-allergen $FEV_1$ values measured at days 41 and 83. There was a significant increase in methacholine $PC_{20}$ on days 83 and 85 with AMG 157 compared to placebo (p<0.05). The allergen-induced shift in methacholine $PC_{20}$ (day 41 to 43, and day 83 to 85) was numerically lower with AMG 157 treatment with an increase of 0.76 and 0.49 doubling doses for AMG 157 relative to placebo, respectively; however, this difference was not statistically significant compared to placebo (FIG. 2). There was no effect of AMG 157 on total IgE or the quantifiable serum markers in the HumanMAP®v. 2.0 panel. Interleukins 4, 5, and 13 and TNF levels were below level of quantitation in >95% of samples.

Geometric mean Th2/Th1 ratio (95% Confidence Intervals) was measured in samples from treated patients. Treatment with AMG 157 was associated with a Th2/Th1 cell ratio numerically but not statistically lower than placebo (The p-value's from the ANOVA were 0.058 for the main effect of treatment, and 0.367 for the treatment by time interaction). The decrease in Th2/Th1 ratio was driven mostly by a decrease in Th2 cells. Blood samples were collected in sodium heparin vacutainers and laboratory procedures initiated within 24 hours of collection. To classify subsets of cytokine-producing cells, whole blood was first activated with phorbol 12-myristate 13-acetate (PMA) and ionomycin in the presence of the protein transport inhibitor brefeldin A. Specifically, 10 uL of leukocyte activation cocktail (LAC, BD Biosciences, San Jose, Calif.) was mixed with 500 uL RPMI and then combined 1-1 with whole blood in a 15 mL tube (BD Falcon). The LAC stimulation level was chosen because it was found to be above EC90 during establishment of the assay (comparing to titrated PMA/Ionomycin). Sample aliquots incubated similarly in the presence of brefeldin A (BD GolgiStop) alone in RPMI were included as negative controls. After a 4 hour incubation at 37° C. and an overnight hold at 18° C., surface and intracellular staining procedures were performed.

Intracelluar cytokine analysis included IFN-γ (BD, clone 25723.11 FITC) and combined analysis of IL-4 (BD, clone 3010.211 PE), IL-5 (BD, clone JES1-39D10 PE) and IL-13 (BD clone JES10-5A2 PE). Fluorescence data were acquired on a validated BD FACSCanto II flow cytometer and analysis was performed in FCS Express software (De Novo, Los Angeles Calif.) using a standardized template. Th1 cells were identified as CD3⁺CD8⁻ T-cells expressing IFN-γ, but not IL-4, IL-5 or IL-13 and Th2 cells were identified as CD3⁺CD8⁻ T-cells expressing IL-4, IL-5 or IL-13, but not IFN-γ. The key end point was the ratio of Th2 to Th1 cells before and after AMG 157 treatment.

The percent of Th1, Th2 and ratio of Th2/Th1 cells were analyzed after log transformation in a baseline-adjusted mixed effects model including post-dose study visit, treatment group and the interaction between visit and treatment along with subject as a random factor. Baseline values were included as a covariate. Only Days 41 and 83 were considered for statistical analysis in order to test for potential Th2/Th1 ratio changes at time-points with AMG 157 exposure. An ANOVA was used to assess whether the treatment groups differed when averaged across all visits (dose term) or at any given time (visit by treatment interaction term). Confidence intervals in the figures have been adjusted for the number of means estimated (Dunn-Sidak). *P<0.05 compared to placebo.

The circulating Th2/Th1 cell ratios were reduced with AMG 157 treatment relative to placebo with reduction of 29% on day 41 (P=0.016) and 23% on day 83 (P=0.47) (Table 1)

TABLE 1

Th2/Th1 Cell Ratio: Intracellular cytokine assay

| Day | Placebo | AMG157 | Treatment Difference Estimate | 95% Confidence Intervals |
|---|---|---|---|---|
| Day 41 | 0.093 | 0.066 | 0.713 | (0.55, 0.93) |
| Day 83 | 0.084 | 0.073 | 0.866 | (0.58, 1.30) |

Safety

Treatment with AMG 157 was not associated with changes in measured lab values, temperature, blood pressure, pulse or respiration. There were 12 adverse events with placebo treatment and 15 adverse events with AMG 157. There were no serious adverse events or deaths. One placebo-treated participant and no AMG 157-treated participants tested positive for anti-AMG 157 antibodies.

Discussion

This study has demonstrated that treatment with monoclonal antibody AMG 157 attenuated most measures of allergen-induced bronchoconstriction (EAR and LAR), along with markers of systemic and airway inflammation in stable allergic asthmatic participants. As such, the weight of data is consistent with the documented role of TSLP in inducing allergen-induced airway responses in murine models.[21] AMG 157 also reduced all of the inflammatory variables measured in the baseline assessment, for the duration of the study, including indices of airway inflammation (F$_E$NO and sputum eosinophils), as well as systemic inflammation (circulating eosinophils). Whether the changes in eosinophils are responsible for attenuation of allergen-induced bronchoconstriction is unknown. This proof-of-concept study suggests that TSLP is not only a pivotal cytokine in allergen-induced airway responses, but also in causing persisting airway inflammation in patients with allergic asthma.

TSLP has been identified as a "master switch" for allergic inflammation in murine models.[22] Higher levels of TSLP were produced in epithelial cells from asthmatic versus healthy individuals,[11] and polymorphisms in the TSLP gene have been associated with both childhood and adult allergic asthma.[13,23] TSLP strongly induced the expression of human major histocompatibility complex I and II and co-stimulatory molecules such as CD40, CD80 and CD86 on myeloid dendritic cells.[6] Induction of TSLP preceded the infiltration of dendritic cells into the skin during allergen-induced late cutaneous responses.[24] TSLP can also induce human mast cell Th2 cytokine production.[8] TSLP may additionally play a role in virus-mediated processes.[25]

TSLP is thought to cause airway and blood eosinophilia in allergic asthmatics through activation of airway dendritic cells and increases in the numbers of Th2 cells, with the production of pro-inflammatory cytokines, including interleukin-5 and interleukin-13.[21] TSLP has also been shown to influence production of interleukin-5 and interleukin-13 from mast cells,[8] CD34$^+$ progenitors[9] and, most recently, type 2 innate lymphoid cells.[26] Inhibition of interleukin-5 has been previously shown to prevent allergen-induced airway eosinophilia[27] which supports this hypothesis. Other airway epithelial-derived cytokines, particularly interleukin-25 and interleukin-33, have also been implicated in allergen-induced airway inflammation in murine models,[28] but there currently is no direct evidence implicating them in allergic asthma in humans.

Epidemiological evidence supports an important role for environmental allergens in the pathobiology of childhood asthma.[29] Allergen inhalation by allergic asthmatics results in many manifestations of asthma, including reversible airflow obstruction, airway hyperresponsiveness[30] and eosinophilic and basophilic airway inflammation.[31] Allergen inhalation challenge has been a valuable clinical model for the study of the mechanisms of allergic asthma and the evaluation of potential new treatments.[20,32] However, allergen inhalation is not responsible for the development or persistence of asthma in many asthmatics, who are non-allergic, or who are not exposed to allergens. Therefore, the importance of TSLP in persisting airway inflammation in these patients cannot be extrapolated from the current study. However, pharmacological attenuation of allergen-induced airway responses in allergic asthmatic participants has previously been associated with effective asthma treatments, even in non-allergic subjects.[5]

Histamine and cysteinyl leukotrienes from airway mast cells and basophils contribute the major part of the EAR and LAR.[33,34] The LAR is also caused by the allergen-induced influx of inflammatory cells, particularly basophils and eosinophils.[31,33] Therefore, AMG 157 likely attenuates these responses through effects both on mast cell activation and inflammatory cell recruitment.

For safety reasons and to avoid the potential modification of allergen-induced airway responses by maintenance treatments such as inhaled corticosteroids or leukotriene receptor antagonists, this study was conducted in stable, allergic asthmatics who were not on regular maintenance asthma treatment with near normal baseline pulmonary function. As in other studies evaluating this patient population,[20,32,33] the participants had evidence of airway inflammation at the time of study enrolment, with increased F$_E$NO and sputum eosinophilia. The mechanism causing persistent airway inflammation in these stable asthmatics is not known. Some may be regularly exposed to ubiquitous allergens, such as house-dust mite, but this accounted for less than half of the participants studied (FIG. 2). Also, because the participants had near normal baseline FEV$_1$ values, it was not possible to observe improvement in baseline FEV$_1$.

All currently available asthma treatments attenuate components of allergen-induced airway responses. However, only inhaled corticosteroids attenuate baseline airway levels of F$_E$NO and eosinophils,[35] as well as allergen-induced increases in these parameters.[36] This study indicates that targeting TSLP can reduce baseline F$_E$NO, and blood and airway eosinophilia. Some patients with severe refractory asthma have persisting airway eosinophilia despite treatment with high-dose inhaled and oral corticosteroids. Targeting the Th2 cytokines interleukin-5, interleukin-13, and interleukin-4 has improved several asthma parameters. Targeting interleukin-5 in patients with severe refractory asthma reduced asthma exacerbations and allowed a reduction in maintenance doses of oral corticosteroids.[37,38] These studies suggest that persisting airway eosinophilia is an important mechanism for some patients with severe refractory asthma. Antibodies directed against interleukin-13 have been shown to improve lung function in asthmatics with a "Th2 phenotype", as indicated by elevated levels of circulating periostin.[39] In addition, an antibody directed against the interleukin-4-receptor-α, the common component of the interleukin-4 and interleukin-13 receptors, allowed removal of maintenance treatment with a combination of inhaled corticosteroids and long-acting $\beta_2$ agonist without a deterioration of asthma control.[40] The production of each of these pro-inflammatory cytokines may be a consequence (downstream) of epithelial cell TSLP production and dendritic cell activation, suggesting that targeting TSLP may also provide benefit in these patient populations. However, further clinical studies will be needed to evaluate this potential benefit.

In summary, treatment for 12 weeks with AMG 157 reduced baseline FeNO and blood and sputum eosinophils in allergic asthmatic participants. This treatment also attenuated allergen-induced changes in these inflammatory parameters, as well as the EAR and LAR. These results support further work on mechanisms of action and investigation of the clinical benefit of AMG 157 in patients with poorly controlled asthma.

Example 2

To determine the Th2/Th1 ratios in Example 1 a methodology was used in which intracellular cytokine staining was performed to determine the ratio of cells expressing Th2 cytokines, such as IL-4, IL-5 and IL-13, compared to those expressing Th1 cytokines, IFN-g, TNF-a and/or IL-2.

In order to maximize the detection of Th2-related cytokines, each of the IL4, IL-5 and IL-13 cytokines were detected using anti-cytokine antibodies labelled with a phycoerythrin (PE) fluorophore. The individual and collective measurement of these cytokines was compared to the level of IFN-g in the same cell population, which is indicative of Th1 cells.

Percentages of cytokine producing cells are set out in Table 2.

TABLE 2

| Panel | Profile | Mean | SD | Median | Min | Max |
|---|---|---|---|---|---|---|
| Panel 1 | IL-4-5-13+ (IFN-g−) | 3.4 | 0.5 | 3.6 | 2.7 | 4.0 |
| | IFN-g+ (IL-4-5-13−) | 32.1 | 11.5 | 28.6 | 21.6 | 46.3 |
| | IL-17A+ (IL-4-5-13−) | 3.6 | 0.7 | 3.5 | 2.7 | 4.6 |
| | IL-2+ (IL-4-5-13−) | 54.0 | 9.4 | 56.1 | 41.7 | 65.6 |
| Panel 2 | IL-4+ (IFN-g−) | 4.9 | 0.6 | 4.8 | 4.0 | 5.9 |
| | IL-5+ (IFN-g−) | 1.8 | 1.4 | 1.5 | 0.7 | 4.5 |
| | IL-13+ (IFN-g−) | 2.3 | 0.3 | 2.2 | 2.0 | 2.7 |
| | IFN-g+ (IL-13−) | 30.6 | 10.2 | 17.7 | 17.7 | 42.3 |

The Table is a result of six donors and the mean, max and min number of cells provided. Th are defined in this assay as a percentage of CD3+CD8− lymphocytes expressing cytokine(s) indicated.

The data could also be expressed as numbers of cells if relative absolute T-cell count is determined in parallel. In certain embodiments, reference counting beads are used to determine cell counts for normalization.

Figure 4:
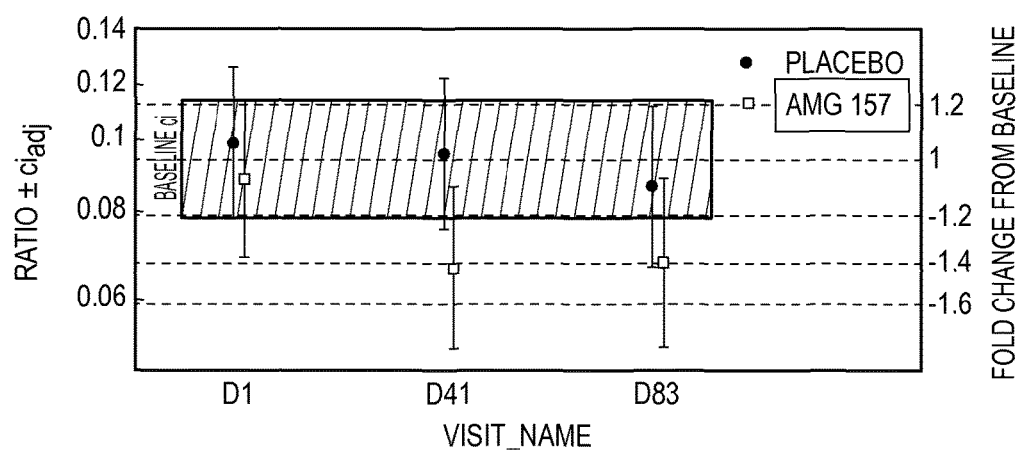
FIG. 4 shows the pharmacological skewing away from the Th2 phenotype in asthma patients receiving anti-TSLP therapy.

The increased signal to noise ratio (S/N) in Panel 1 suggests an advantage of using combined measurement of IL-4-5-13 for detection of Th2 cells. IL-4, IL-5 and IL-13 are largely expressed by the same cells, which is especially true for IL-5 and IL-13. Results of analysis are set out in Table 3. Results are also set out graphically in FIG. 4 and show a skewing away from Th2 in treated patients.

TABLE 3

| Panel | Profile | Mean | SD | Median | Min | Max |
|---|---|---|---|---|---|---|
| Panel 1 | IL-4-5-13+ (IFN-g−) | 13.0 | 4.2 | 11.6 | 8.3 | 19.8 |
| | IFN-g+ (IL-4-5-13−) | 177.9 | 79.3 | 169.2 | 100.0 | 285.7 |
| | IL-17A+ (IL-4-5-13−) | 38.8 | 8.6 | 41.8 | 21.5 | 44.5 |
| | IL-2+ (IL-4-5-13−) | 41.7 | 8.9 | 40.3 | 32.3 | 54.3 |
| Panel 2 | IL-4 S/N (IFN-g−) | 6.3 | 1.3 | 6.0 | 5.1 | 8.6 |
| | IL-5 S/N (IFN-g−) | 5.3 | 0.4 | 5. | 5.0 | 6.1 |
| | IL-13 S/N (IFN-g−) | 8.1 | 2.1 | 2 | 6.6 | 12.1 |
| | IFN-g+ (IL-13−) | 152.9 | 47.4 | 7.2 | 89.2 | 217.6 |

Example 3

Figure 5A:
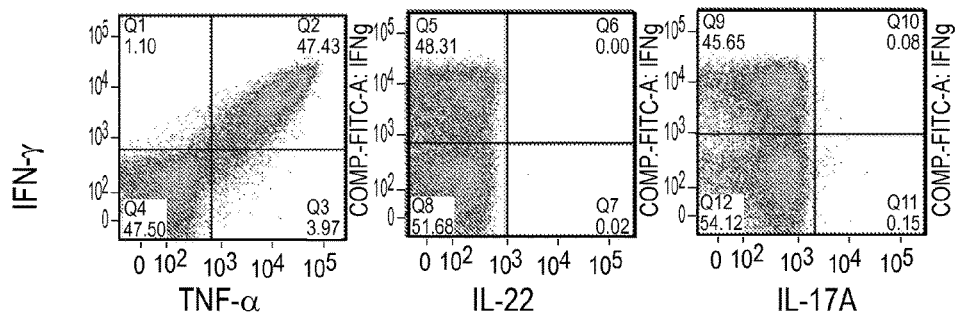
FIGS. 5A to 5B show the cytokine profile of cells taken from an SCLE patient when unstimulated (FIG. 5A) and stimulated (FIG. 5B) with PMA/ionomycin.
Figure 5B:
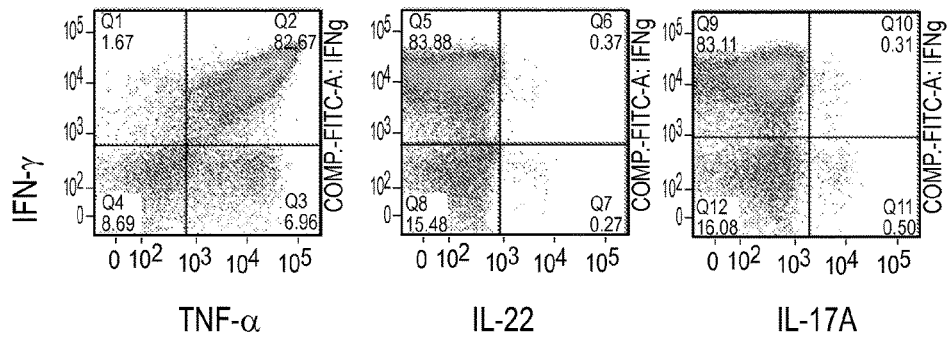

This present method was used to evaluate samples from psoriasis, and subacute cutaneous lupus (SCLE) patients to look for impact on Th17 cells. A SCLE sample was unique in that unstimulated controls showed high levels of IFN-g and TNF-a, suggesting this assay may be useful as a diagnostic tool to guide treatment for patients suffering from different types of lupus-related diseases (FIG. 5).

Numerous modifications and variations in the invention as set forth in the above illustrative examples are expected to occur to those skilled in the art. Consequently only such limitations as appear in the appended claims should be placed on the invention.

All publications and patent documents cited in this application are incorporated by reference in their entirety to the same extent as if the contents of each individual publication or patent document were incorporated herein.

REFERENCES

1. Ferreira M A, Matheson M C, Tang C S, et al. Genome-wide association analysis identifies 11 risk variants associated with the asthma with hay fever phenotype. J Allergy Clin Immunol 2013.
2. Boulet L P, Cartier A, Thomson N C, Roberts R S, Dolovich J, Hargreave F E. Asthma and increases in nonallergic bronchial responsiveness from seasonal pollen exposure. J Allergy Clin Immunol 1983; 71:399-406.
3. Green R M, Custovic A, Sanderson G, Hunter J, Johnston S L, Woodcock A. Synergism between allergens and viruses and risk of hospital admission with asthma: case-control study. BMJ 2002; 324:763.
4. Inman M D, Ellis R, Wattie J, Denburg J A, O'Byrne P M. Allergen-induced increase in airway responsiveness, airway eosinophilia, and bone-marrow eosinophil progenitors in mice. Am J Respir Cell Mol Biol 1999; 21:473-9.
5. Diamant Z, Gauvreau G M, Cockcroft D W, et al. Inhaled allergen bronchoprovocation tests. J Allergy Clin Immunol 2013; 132:1045-55.
6. Soumelis V, Reche P A, Kanzler H, et al. Human epithelial cells trigger dendritic cell mediated allergic inflammation by producing TSLP. Nat Immunol 2002; 3:673-80.
7. Reche P A, Soumelis V, Gorman D M, et al. Human thymic stromal lymphopoietin preferentially stimulates myeloid cells. J Immunol 2001; 167:336-43.
8. Allakhverdi Z, Comeau M R, Jessup H K, et al. Thymic stromal lymphopoietin is released by human epithelial cells in response to microbes, trauma, or inflammation and potently activates mast cells. J Exp Med 2007; 204:253-8.

9. Allakhverdi Z, Comeau M R, Smith D E, et al. CD34+ hemopoietic progenitor cells are potent effectors of allergic inflammation. J Allergy Clin Immunol 2009; 123:472-8.
10. Ying S, O'Connor B, Ratoff J, et al. Thymic stromal lymphopoietin expression is increased in asthmatic airways and correlates with expression of Th2-attracting chemokines and disease severity. J Immunol 2005; 174: 8183-90.
11. Ying S, O'Connor B, Ratoff J, et al. Expression and cellular provenance of thymic stromal lymphopoietin and chemokines in patients with severe asthma and chronic obstructive pulmonary disease. J Immunol 2008; 181: 2790-8.
12. He J Q, Hallstrand T S, Knight D, et al. A thymic stromal lymphopoietin gene variant is associated with asthma and airway hyperresponsiveness. J Allergy Clin Immunol 2009; 124:222-9.
13. Harada M, Hirota T, Jodo A I, et al. Thymic stromal lymphopoietin gene promoter polymorphisms are associated with susceptibility to bronchial asthma. Am J Respir Cell Mol Biol 2011; 44:787-93.
14. O'Byrne P M, Dolovich J, Hargreave F E. Late asthmatic responses. Am Rev Respir Dis 1987; 136:740-51.
15. Cockcroft D W, Murdock K Y, Kirby J, Hargreave F. Prediction of airway responsiveness to allergen from skin sensitivity to allergen and airway responsiveness to histamine. Am Rev Respir Dis 1987; 135:264-7.
16. Pizzichini E, Pizzichini M M, Efthimiadis A, et al. Indices of airway inflammation in induced sputum: reproducibility and validity of cell and fluid-phase measurements. Am J Respir Crit Care Med 1996; 154:308-17.
17. American Thoracic S, European Respiratory S. ATS/ERS recommendations for standardized procedures for the online and offline measurement of exhaled lower respiratory nitric oxide and nasal nitric oxide, 2005. Am J Respir Crit Care Med 2005; 171:912-30.
18. Inman M D, Watson R, Cockcroft D W, Wong B J, Hargreave F E, O'Byrne P M. Reproducibility of allergen-induced early and late asthmatic responses. J Allergy Clin Immunol 1995; 95:1191-5.
19. Gauvreau G M, Watson R M, Rerecich T J, Baswick E, Inman M D, O'Byrne P M. Repeatability of allergen-induced airway inflammation. J Allergy Clin Immunol 1999; 104:66-71.
20. Gauvreau G M, Boulet L P, Cockcroft D W, et al. Effects of interleukin-13 blockade on allergen-induced airway responses in mild atopic asthma. Am J Respir Crit Care Med 2011; 183:1007-14.
21. Zhou B, Comeau M R, De Smedt T, et al. Thymic stromal lymphopoietin as a key initiator of allergic airway inflammation in mice. Nat Immunol 2005; 6:1047-53.
22. Liu Y J. Thymic stromal lymphopoietin: master switch for allergic inflammation. J Exp Med 2006; 203:269-73.
23. Bunyavanich S, Melen E, Wilk J B, et al. Thymic stromal lymphopoietin (TSLP) is associated with allergic rhinitis in children with asthma. Clin Mol Allergy 2011; 9:1.
24. Corrigan C J, Jayaratnam A, Wang Y, et al. Early production of thymic stromal lymphopoietin precedes infiltration of dendritic cells expressing its receptor in allergen-induced late phase cutaneous responses in atopic subjects. Allergy 2009; 64:1014-22.
25. Kato A, Favoreto S, Jr., Avila P C, Schleimer R P. TLR3- and Th2 cytokine-dependent production of thymic stromal lymphopoietin in human airway epithelial cells. J Immunol 2007; 179:1080-7.
26. Mjosberg J, Bernink J, Golebski K, et al. The transcription factor GATA3 is essential for the function of human type 2 innate lymphoid cells. Immunity 2012; 37:649-59.
27. Leckie M J, ten Brinke A, Khan J, et al. Effects of an interleukin-5 blocking monoclonal antibody on eosinophils, airway hyper-responsiveness, and the late asthmatic response. Lancet 2000; 356:2144-8.
28. Gavala M L, Bashir H, Gem J E. Virus/allergen interactions in asthma. Curr Allergy Asthma Rep 2013; 13:298-307.
29. Sears M R, Burrows B, Flannery E M, Herbison G P, Holdaway M D. Atopy in childhood. I. Gender and allergen related risks for development of hay fever and asthma. Clin Exp Allergy 1993; 23:941-8.
30. Gauvreau G M, Watson R M, O'Byrne P M. Kinetics of allergen-induced airway eosinophilic cytokine production and airway inflammation. Am J Respir Crit Care Med 1999; 160:640-7.
31. Gauvreau G M, Lee J M, Watson R M, Irani A M, Schwartz L B, O'Byrne P M. Increased numbers of both airway basophils and mast cells in sputum after allergen inhalation challenge of atopic asthmatics. Am J Respir Crit Care Med 2000; 161:1473-8.
32. Gauvreau G M, Boulet L P, Cockcroft D W, et al. OX40L blockade and allergen-induced airway responses in subjects with mild asthma. Clin Exp Allergy 2014; 44:29-37.
33. Davis B E, Illamperuma C, Gauvreau G M, et al. Single-dose desloratadine and montelukast and allergen-induced late airway responses. Eur Respir J 2009; 33:1302-8.
34. Parameswaran K, Liang H, Fanat A, Watson R, Snider D P, O'Byrne P M. Role for cysteinyl leukotrienes in allergen-induced change in circulating dendritic cell number in asthma. J Allergy Clin Immunol 2004; 114:73-9.
35. Nolte H, Pavord I, Backer V, et al. Dose-dependent anti-inflammatory effect of inhaled mometasone furoate/formoterol in subjects with asthma. Respir Med 2013; 107:656-64.
36. Dahlen B, Lantz A S, Ihre E, et al. Effect of formoterol with or without budesonide in repeated low-dose allergen challenge. Eur Respir J 2009; 33:747-53.
37. Nair P, Pizzichini M M, Kjarsgaard M, et al. Mepolizumab for prednisone-dependent asthma with sputum eosinophilia. N Engl J Med 2009; 360:985-93.
38. Haldar P, Brightling C E, Hargadon B, et al. Mepolizumab and exacerbations of refractory eosinophilic asthma. N Engl J Med 2009; 360:973-84.
39. Corren J, Lemanske R F, Hanania N A, et al. Lebrikizumab treatment in adults with asthma. N Engl J Med 2011; 365:1088-98.
40. Wenzel S, Ford L, Pearlman D, et al. Dupilumab in persistent asthma with elevated eosinophil levels. N Engl J Med 2013; 368:2455-66.

What is claimed:
1. A method for detecting a ratio of T helper 2 (Th2) and T helper 1 (Th1) cells in a sample from a patient comprising measuring levels of Th2-specific and Th1-specific cytokines, the method comprising:
  a) contacting the sample with
    i) two or more specific binding agents that bind two or more Th2 cytokines, wherein the two or more specific binding agents for the Th2-specific cytokines are labeled with a first fluorophore; and
    ii) at least one specific binding agent that binds a Th1 cytokine, wherein the specific binding agent for the Th1 cytokine is labeled with a second fluorophore that is different from the first fluorophore;

b) measuring levels of the first and second fluorophores in the sample and designating the cell as a Th1 or Th2 cell based on the level of Th1-specific and Th2-specific fluorophore detected; and c) determining the ratio of Th2 to Th1 cells in a sample.

2. The method of claim 1 further comprising determining the ratio of Th1, Th2 and Th17 cells in the sample, comprising a) contacting the sample with iii) at least one specific binding agent that binds a Th17 cytokine, wherein the specific binding agent for the Th17 cytokine is labeled with a second fluorophore that is different from the first fluorophore or labeled with a third fluorophore;

b) measuring levels of the first, second and/or third fluorophores in the sample and designating the cell as a Th1, Th2 or Th17 cell based on the level of Th1-specific, Th2-specific or Th17-specific fluorophore detected; and c) determining the ratio of Th1 to Th2 to Th17 cells in a sample.

3. The method of claim 2, wherein the Th17 cytokines are selected from the group consisting of IL-17A, IL-17F, IFN-g and IL-22.

4. The method of claim 2, wherein the specific binding agent is an antibody specific for a Th17-specific cytokine.

5. The method of claim 1, wherein the Th2 cytokines are selected from the group consisting of IL-4, IL-5 and IL-13.

6. The method of claim 1, wherein the Th1 cytokines are selected from the group consisting of interferon gamma (IFN-g), tumor necrosis factor alpha (TNF-a) and IL-2.

7. The method of claim 1, wherein the specific binding agent is an antibody specific for a Th1-specific or Th2-specific cytokine.

8. The method of claim 1, wherein the patient is suffering from a disease or disorder selected from the group consisting of asthma, allergic rhinosinusitis, allergic conjunctivitis, atopic dermatitis, fibrotic disorders, Systemic Lupus Erythematosus (SLE), multiple sclerosis and cancer.

9. The method of claim 1, wherein the sample is obtained before and/or after treatment with a therapeutic agent.

10. The method of claim 1, wherein the therapeutic agent is an antibody specific for thymic stromal lymphopoietin (TSLP).

11. The method of claim 1, wherein the first fluorophore is phycoerythrin (PE) and the second flurophore is fluorescein isothiocyanate (FITC).

12. The method of claim 1, wherein the sample is whole blood, peripheral blood mononuclear cells, cerebrospinal fluid, bronchioalveolar lavage, nasal lavage, induced sputum or a biopsy from the patient.

13. The method of claim 1, wherein the cytokines are contacted intracellularly.

14. A method for detecting a ratio of T helper 1 (Th1) and T helper 17 (Th17) cells in a sample from a patient comprising measuring levels of Th1-specific and Th17-specific cytokines, the method comprising:

a) contacting the sample with i) two or more specific binding agents that bind two or more Th17 cytokines, wherein the two or more specific binding agents for the Th17-specific cytokines are labeled with a first fluorophore; and ii) at least one specific binding agent that binds a Th1 cytokine, wherein the specific binding agent for the Th1 cytokine is labeled with a second fluorophore that is different from the first fluorophore;

b) measuring levels of the first and second fluorophores in the sample and designating the cell as a Th1 or Th17 cell based on the level of Th1-specific and Th17-specific fluorophore detected; and c) determining the ratio of Th1 to Th17 cells in a sample.

15. A method for detecting a ratio of T helper 2 (Th2) and T helper 17 (Th17) cells in a sample from a patient comprising measuring levels of Th2-specific and Th17-specific cytokines, the method comprising:

a) contacting the sample with i) two or more specific binding agents that bind two or more Th2 cytokines, wherein the two or more specific binding agents for the Th2-specific cytokines are labeled with a first fluorophore; and ii) at least one specific binding agent that binds a Th17 cytokine, wherein the specific binding agent for the Th17 cytokine is labeled with a second fluorophore that is different from the first fluorophore;

b) measuring levels of the first and second fluorophores in the sample and designating the cell as a Th2 or Th17 cell based on the level of Th2-specific and Th17-specific fluorophore detected; and c) determining the ratio of Th2 to Th17 cells in a sample.

16. A method for identifying a sub-population of asthma patients responsive to treatment with a therapeutic agent comprising measuring the baseline ratio of T helper 2 (Th2) and T helper 1 (Th1) cells in a patient sample or changes in the ratio after administration of the therapeutic agent, the method comprising:

a) contacting the sample with i) two or more specific binding agents that bind two or more Th2-specific cytokines, wherein the two or more specific binding agents for the Th2-specific cytokines are labeled with a first fluorophore; and ii) at least one specific binding agent that binds a Th1-specific cytokine, wherein the specific binding agent for the Th1-specific cytokine is labeled with a second fluorophore that is different from the first fluorophore;

b) measuring levels of the first and second fluorophores in the sample and designating the cell as a Th1 or Th2 cell based on the level of Th2-specific and Th1-specific fluorophore detected; and c) determining the ratio of Th2 to Th1 cells in a sample based on the level of Th2-specific cytokine and Th1-specific cytokine detected, wherein the patient is identified as responsive to the therapeutic agent if the ratio of Th2 cells/Th1 cells decreases; and d) altering treatment with the therapeutic agent if the patient is determined to be non-responsive to the therapeutic agent or maintaining the dose of therapeutic agent if the patient is determined to be responsive to treatment with the therapeutic agent.

17. The method of claim 16, wherein the therapeutic agent is an anti-TSLP antibody.

18. The method of claim 16, wherein the therapeutic agent is administered for one week, two weeks, three weeks, four weeks, six weeks, two months, three months or more prior to obtaining the sample.

19. The method of claim 16, wherein the patient is identified as responsive to treatment if the ratio of Th2/Th1 cells decreases by 20%, 30%, 40%, 50%, 60% or more.

20. The method of claim 16, a Th2/Th1 ratio at which the patient is identified as responsive to treatment is approximately 0.1 or below.

21. A method of altering the dose regimen of an anti-thymic stromal lymphopoietin (TSLP) agent in treating an immune disorder comprising determining the ratio of Th2/

Th1 and/or Th17 cells in a sample using the method of claim 1 or 2 and altering the dose of anti-TSLP antibody if the ratio of Th2/Th1 and/or Th17 cells changes during treatment, wherein the dose of therapeutic is increased if the ratio of Th2/Th1 cells is stable or increases indicating skewing towards Th2 profile;

wherein the dose of therapeutic is decreased if the ratio of Th2/Th1 cells decreases indicating reduction in Th2 profile.

22. The method of claim 21 wherein the immune disorder is selected from the group consisting of asthma, allergic rhinosinusitis, allergic conjunctivitis, atopic dermatitis and fibrotic disorders.

23. A method of altering the dose regimen of an asthma therapeutic comprising determining the ratio of Th2/Th1 and/or Th17 cells in a sample using the method of claim 1 or 2 and altering the dose of asthma therapeutic if the ratio of Th2/Th1 and/or Th17 cells changes during treatment, wherein the dose of therapeutic is increased if the ratio of Th2/Th1 cells is stable or increases indicating skewing towards Th2 profile;

wherein the dose of therapeutic is decreased if the ratio of Th2/Th1 cells decreases indicating reduction in Th2 profile.

* * * * *